US010829825B2

(12) United States Patent
Paillier et al.

(10) Patent No.: US 10,829,825 B2
(45) Date of Patent: Nov. 10, 2020

(54) DETECTION OF MECA VARIANT STRAINS OF METHICILLIN-RESISTANT *STAPHYLOCOCCUS AUREUS*

(71) Applicant: bioMerieux S.A., Marcy l'Étoile (FR)

(72) Inventors: Francois Paillier, Saint-Nazaire-les-Eymes (FR); Celine Chambon, Seyssinet-Pariset (FR); Cathy Saint-Patrice, Fontaine (FR)

(73) Assignee: bioMerieux S.A., Marcy l'Étoile (FR)

( * ) Notice: Subject to any disclaimer, the term of this patent is extended or adjusted under 35 U.S.C. 154(b) by 343 days.

(21) Appl. No.: 15/177,973

(22) Filed: Jun. 9, 2016

(65) Prior Publication Data
US 2016/0281144 A1 Sep. 29, 2016

Related U.S. Application Data

(62) Division of application No. 13/725,364, filed on Dec. 21, 2012, now Pat. No. 9,394,573.

(30) Foreign Application Priority Data

Dec. 23, 2011 (EP) .................................... 11306776

(51) Int. Cl.
*C12P 19/34* (2006.01)
*C12Q 1/689* (2018.01)
(52) U.S. Cl.
CPC ......... *C12Q 1/689* (2013.01); *C12Q 2600/16* (2013.01)
(58) Field of Classification Search
CPC ............................ C12Q 1/689; C12Q 2600/16
USPC ........................................................ 435/91.2
See application file for complete search history.

(56) References Cited

U.S. PATENT DOCUMENTS

| 5,702,895 | A | 12/1997 | Matsunaga et al. | |
|---|---|---|---|---|
| 6,156,507 | A | 12/2000 | Hiramatsu et al. | |
| 6,379,897 | B1 | 4/2002 | Weidenhammer et al. | |
| 7,449,289 | B2 * | 11/2008 | Huletsky ................ | C12Q 1/689 435/6.15 |
| 7,888,075 | B2 | 2/2011 | McCarthy et al. | |
| 8,367,337 | B2 | 2/2013 | Jay et al. | |
| 2004/0076990 | A1 | 4/2004 | Picard et al. | |
| 2005/0019893 | A1 | 1/2005 | Huletsky et al. | |
| 2006/0057613 | A1 | 3/2006 | Ramakrishnan et al. | |
| 2007/0054296 | A1 | 3/2007 | Piepenburg et al. | |
| 2007/0082340 | A1 | 4/2007 | Huletsky et al. | |
| 2008/0227087 | A1 | 9/2008 | Huletsky et al. | |
| 2009/0081663 | A1 | 3/2009 | Paitan | |
| 2012/0165229 | A1 * | 6/2012 | Reiske ................... | C12Q 1/689 506/16 |

FOREIGN PATENT DOCUMENTS

| EP | 0887424 A2 | 12/1998 |
|---|---|---|
| EP | 1 529 847 B1 | 4/2006 |
| WO | WO 97/31125 A2 | 8/1997 |
| WO | WO 02/099034 A2 | 12/2002 |
| WO | WO 2006/111028 A1 | 10/2006 |
| WO | WO 2008/080620 | 7/2008 |
| WO | WO 2008/129428 A2 | 10/2008 |
| WO | WO 2009/018000 A1 | 2/2009 |
| WO | WO 2009/090310 A1 | 7/2009 |
| WO | 2012/078773 A2 | 6/2012 |

OTHER PUBLICATIONS

Ito et al., Antimicrobial agents and chemotherapy, 45 (5), 1323-1336, May (Year: 2001).*
Biohelix, IsoAmp® Rapid mecA Detection Kit, 2 Pages, Retrieved from the internet on May 25, 2013 at URL http://www.biohelix.com/pdf/D0200E_mecA_eDatacard.pdf.
Biohelix, IsoAmp® Rapid Staph Detection Kit, 2 Pages, Retrieved from the Internet on May 25, 2013 at URL http://www.biohelix.com/pdf/D0100E_SA_eDatacard.pdf.
Bishop et al., "Concurrent Analysis of Nose and Groin Swab Specimens by the IDI-MRSA PCR Assay is Comparable to Analysis by Individual-Specimen PCR and Routine Culture Assays, for Detection of Colonization by Methicillin-Resistant *Staphylococcus aureus*," *J. Clin. Microbiol.* 44(8):2904-2908 (2006).
Brown et al., "Real-Time PCR Detection of *S. aureus* and MRSA from Wound, Fluid and Respiratory Samples," Abstract No. C-077. American Society for Microbiology Conference, Orlando, Florida, May 21-25, 2006.
Chinese Patent Application No. 200880123825.5, Filed: Dec. 19, 2008; office action dated Jun. 5, 2012.
Cuny et al., "PCR for the identification of methicillin-resistant *Staphylococcus aureus* (MRSA) strains using a single primer pair specific for SCCmec elements and the neighbouring, chromosome-borne orfX," Clin. Microbiol. Infect. 11:834-837 (2005).
Desjardins et al., "Evaluation of the IDI-MRSA Assay for Detection of Methicillin-Resistant *Staphylococcus aureus* from Nasal and Rectal Specimens Pooled in a Selective Broth," *J. Clin. Microbiol.* 44(4):1219-1223 (2006).
Donnio et al., "Partial Excision of the Chromosomal Cassette Containing the Methicillin Resistance Determinant Results in Methicillin-Susceptible *Staphylococcus aureus*," J. Clin. Microbiol. 43(8):4191-4193 (2005).
Drews, et al., "Verification of the IDI-MRSA Assay for Detecting Methicillin-Resistant *Staphylococcus aureus* in Diverse Specimen Types in a Core Clinical Laboratory Setting," *J. Clin. Microbiol.* 44(10):3794-3796 (2006).
European Application No. 08868000.4, filed Dec. 19, 2008; extended European search report dated Feb. 28, 2011.
European Application No. 08868000.4, filed Dec. 19, 2008; office action dated Jan. 13, 2012.

(Continued)

*Primary Examiner* — Cynthia B Wilder
(74) *Attorney, Agent, or Firm* — Myers Bigel, P.A.

(57) ABSTRACT

The present invention provides improved tests for the detection: of methicillin-resistant *Staphylococcus aureus* bearing a variant mecA gene. The tests are particularly useful for eliminating certain false negative results due to the presence of this variant in MRSA in patient samples.

20 Claims, 2 Drawing Sheets
Specification includes a Sequence Listing.

(56) References Cited

OTHER PUBLICATIONS

Goldmeyer J. et al., "Identification of *Staphylococcus aureus* and Determination of Methicillin Resistance Directly from Positive Blood Cultures by Isothermal Amplification and a Disposable Detection Device", *Journal of Clinical Microbiology*, 2008, 46(4):1534.
Hagen et al., "Development of a real-time PCR assay for rapid identification of methicillin-resistant *Staphylococcus aureus* from clinical Samples," Int. J. Med. Microbiol. 295:77-86 (2005).
Holfelder et al., "Direct detection of methicillin-resistant *Staphylococcus aureus* in clinical specimens by a nucleic acid-based hybridisation assay," Clin. Microbiol. Infect. 12:1163-1167 (2006).
Huletsky et al., "Identification of methicillin-resistant *Staphylococcus aureus* carriage in less than 1 hour during a hospital surveillance program," Clin. Infect. Dis. 40:976-981 (2005).
Huletsky et al., New Real-Time PCR Assay for Rapid Detection of Methicillin-Resistant *Staphylococcus aureus* Directly from Specimens Containing a Mixture of Staphylococci, *J. Clin. Microbiol.* 42(5):1875-1884 (2004).
International Search Report and Written Opinion, PCT/US08/13922, dated Aug. 5, 2009.
Israeli Patent Application No. 206499; Filed: Dec. 19, 2008; office action dated Mar. 5, 2012.
Ito T. et al., "Guidelines for Reporting Novel mecA Gene Homologues", *Antimicrob. Agents Chemother.*, published online ahead of print on Aug. 6, 2012, 9 pages.
Laurent F. et al., "MRSA Harboring mecA Variant Gene mecC, France", *Emerging Infectious Diseases*, vol. 18, No. 9, Sep. 2012, 1465-1467.
Lowe T. et al. "A computer program for selection of oligonucleotide primers for polymerase chain reactions", *Nucleic Acids Research*, 1990, vol. 18(7), p. 1757-1761.
Rupp et al., "Be Aware of the Possibility of False-Positive Results in Single-Locus PCR Assays for Methicillin-Resistant *Staphylococcus aureus*," *J. Clin. Microbiol.* 4(6):2317 (2006).
Warren et al., "Detection of Methicillin-Resistant *Staphylococcus aureus* Directly from Nasal Swab Specimens by a Real-Time PCR Assay," *J. Clin. Microbiol.* 42(12):5578-5581 (2004).
Zhang et al., "Novel multiplex PCR assay for characterization and concomitant subtyping of staphylococcal cassette chromosome mec types I to V in methicillin-resistant *Staphylococcus aureus*," J. Clin. Microbiol. 43:5026-5033 (2005).
Cuny et al. "Rare Occurrence of Methicillin-Resistant *Staphylococcus aureus* CC130 with a Novel mecA Homologue in Humans in Germany" *PloS ONE* 6(9):1-5 e24360 (2011).
GenBank Database Accession FR821779.1 "*Staphylococcus aureus* subsp. *aureus* LGA251 Complete Genome Sequence", Aug. 23, 2011 (first page only).

Garcia-Alvarez et al. "Meticilhin-Resistant *Staphylococcus aureus* with a Novel mecA Homologue in Human and Bovine Populations in the UK and Denmark: a Descriptive Study" *LancetInfect Dis* 11:595-603 (2011).
Pichon et al. "Development of a Real-Time Quadruplex PCR Assay for simultaneous Detection of nuc, Panton-Valentine Leucocidin (PVL), mecA and Homologue mecA$_{LGA251}$" *J Antimicrob Chemother* 67:2338-2341 (2012).
Shore et al. "Detection of Staphylococcal Cassette Chromosome mec Type XI Carrying Highly Divergent mecA, mecl, mecR1, blaZ, and ccr Genes in Human Clinical Isolates of Clonal Complex 130 Methicillin-Resistant *Staphylococcus aureus*" *Antimicrobial Agents and Chemotherapy* 55(8):3765-3773 (2011).
Shore et al. "Seven Novel Variants of the Staphylococcal Chromosomal Cassette mec in Methicillin Resistant *Staphylococcus aureus* Isolates from Ireland" *Antimicrobial Agents and Chemotherapy* 49(5):2070-2083 (2005).
International Search Report and Written Opinion dated Mar. 12, 2013 for PCT International Application No. PCT/EP2012/078856 (13 pages).
Stegger et al. "Rapid detection, differentiation and typing of methicillin-resistant *Staphylococcus aureus* harbouring either mecA or the new mecA homologue mecALGA251", Clin Microbiol Infect 18:395-400 (2011).
Examination Report corresponding to European Application No. 12813030.9 dated Jan. 20, 2016 (8 pages).
Japanese Office Action corresponding to Japanese Application No. 2014-548106 dated Jun. 10, 2018 (14 pages).
Uhlen et al. "Complete Sequence of the Staphylococcal Gene Encoding Protein A", J. Biol. Chem. 259(3):1695-1702 (1984).
Shopsin et al. "Evaluation of Protein A Gene Polymorphic Region DNA Sequencing for Typing of *Staphylococcus aureus* Strains", J. Clin. Microbial. 37(11):3556-3563 (1999).
Strommenger et al. "Assignment of *Staphylococcus* Isolates to Groups by spa Typing, Smal Macrorestriction Analysis, and Multilocus Sequence Typing", J. Clin. Microbial. 44(7):2533 to 2540 (2006).
Soderquist et al. "Real-time multiplex PCR for direct detection of methicillin-resistant *Staphylococcus aureus* (MRSA) in clinical samples enriched by broth culture", APMIS 120:427-432 (2011).
Medhus et al. "Methicillin-resistant *Staphylococcus aureus* with the novel mecC gene variant isolated from a cat suffering from chronic conjunctivitis", J. Antimicrob. Chemother. 68:968-969 (2013).
Rao et al. "Molecular Detection and Surveillance of Healthcare-Associated Infections", Molecular Diagnostics: Techniques and Applications for the Clinical Laboratory Chp. 27:327-340 (2010).
Kondo et al. "Combination of Multiplex PCRs for Staphylococcal Cassette Chromosome mec Type Assignment: Rapid Identification System for mec, ccr, and Major Differences in Junkyard Regions", Antimicrobial Agents and Chemotherapy 51(1):264-274 (2007).

* cited by examiner

DETECTION OF MECA VARIANT STRAINS OF METHICILLIN-RESISTANT *STAPHYLOCOCCUS AUREUS*

STATEMENT OF PRIORITY

This application is a divisional of and claims priority to U.S. patent application Ser. No. 13/725,364, filed Dec. 21, 2012, which claims priority to European Patent Application No. EP11306776.3, filed Dec. 23, 2011, the entire contents of each of which are incorporated by reference herein.

STATEMENT REGARDING ELECTRONIC FILING OF A SEQUENCE LISTING

A Sequence Listing in ASCII text format, submitted under 37 C.F.R, 0 1.821, entitled 9310-162TSDV_ST25.txt, 6,331 bytes in size, generated on Jun. 3,2016 and filed via EPS-Web, is provided in lieu of a paper copy. The Sequence listing is incorporated herein by reference into the specification for its disclosures.

FIELD OF THE INVENTION

The present invention relates to molecular detection of methicillin-resistant *Staphylococcus aureus* (MRSA). More particularly, the present invention relates to an improved detection of MRSA that includes additional strains bearing a variant of the mecA gene.

BACKGROUND OF THE INVENTION

A strain of *Staphylococcus aureus* was shown for the first time in 1961 to be resistant to methicillin. Today, methicillin-resistant *Staphylococcus aureus* (MRSA) is one of the most prevalent antibiotic resistance pathogen causing hospital and community infections. The emergence of MRSA strains is due to the acquisition and insertion of a mobile genetic element, the Staphylococcal Cassette Chromosome mec (SCCmec), into the chromosome of susceptible *S. aureus* strains. Indeed, this SCCmec element carries the mecA gene, which is responsible for methicillin resistance (Staphylococcal Cassette Chromosome mec; Ito et al, 2001, *Antimicrob. Agents Chemother.* 45(5): 1323-1336; Hiramatsu, et al., 2001, *Trends Microbiol.* Oct; 9(10):486-93). The mecA gene encodes for a modified Penicillin Binding Protein called PBP2a or PBP2', Contrary to the native PBP, this PBP2a has a low affinity for the β-lactam antibiotics that permits to continue the synthesis of cell wall even in presence of (β-lactam antibiotics.

SCCmec element can be incorporated into the chromosome of *S. aureus* and other coagulase negative Staphylococci, mainly *S. epidermidis* and *S. haemolyticus*. SCCmec is characterized by the presence of terminal inverted and direct repeats, a set of site-specific recombinase genes (ccrA and ccrB), and the mecA gene complex (Ito et al., 1999, *Antimicrob. Agents Chemother,* 43:1449-1458; Katayama et al., 2000, *Antimicrob. Agents Chemother.* 44:1549-1555). The site of insertion of this mecA gene cassette SCCmec into the *Staphylococcus aureus* genome is known and the sequence conserved (Ito et al, 2001, *Antimicrob. Agents Chemother.* 45:1323-1336). After insertion into the *S. aureus* chromosome, the SCCmec has a left extremity junction and a right extremity junction (see FIG. 1), with a surrounding left extremity junction region and right extremity junction region, respectively, that includes the SCCmec cassette and chromsosomal DNA where the SCCmec sequence is contiguous with the *S. aureus* chromosomal sequence. The nucleotide sequence of the regions surrounding the left and right boundaries of SCCmec DNA (i.e., attL and attR, respectively), as well as those of the regions around the SCCmec DNA integration site (i.e., attBscc, the bacterial chromosome attachment site for SCCmec DNA), have previously been analyzed. Sequence analysis of the integration sites revealed that attBscc is located at the 3' end of a novel open reading frame (ORF), orfX. orfX encodes a polypeptide of 159 amino acids annotated recently as a 23S rRNA methyltransferase (www.uniprot.org/uniprot/Q617F2). Organization of the mecA region of SCCmec has additionally been studied (Oliveira et al., 2000, *Antimicrob. Agents Chemother.* 44(7):1906-1910).

Typically, in an MRSA assay in a patient, a nasal swab is taken from the patient and cultured repeatedly, to determine if an MRSA strain is present. Newer methods are being developed that allow identification of MRSA directly from a nasal swab and in a much shorter amount time. Samples are also evolving, and many papers show the interest to sample several anatomical sites of the same patient to increase the possibility to detect MRSA carriers. The sites could be nasal plus throat, axilla, groin and or perineum. (Methicillin Resistant *Staphylococcus aureus* colonisation at different Body Sites: a Prospective, Quantitative Analysis, Mermel et al. 2011, *Journal of Clinical Microbiology*).

Amplification is a well-known art, and various methods have been developed, including transcription-based amplification such as transcription-mediated amplification (TMA; U.S. Pat. Nos. 5,766,849; 5,399,491; 5,480,784; 5,766,849; and 5,654,142) and nucleic acid sequence-based amplification (NASBA; 5,130,238; 5,409,818; 5,654,142; and 6,312,928), and cycling nucleic acid amplification technologies; (thermocycling) such as polymerase chain reaction (PCR; U.S. Pat. Nos. 4,683,195; 4,965,188 4,683,202) and ligase chain reaction (LOR; U.S. Pat. No. 5,792,607). Known amplification methods also include strand displacement amplification (SDA), self-sustained sequence replication (3SR), Q-B replicase, and cascade rolling circle amplification (CRCA).

Detection methods utilizing nucleic acids are also well known in the art. Nucleic acids are often labeled for various detection purposes. For example, methods described in U.S. Pat. Nos. 4,486,539 (Kourlisky); 4,411,955 (Ward); 4,882, 269 (Schneider) and 4,213,893 (Canico), illustrate preparation of labeled detection probes for detecting specific nucleic acid sequences. Probe designs for different detection methods, such as target-capture, HPA, TaqMan, molecular beacons and sandwich hybridization have also been described (e.g., U.S. Pat. Nos. 4,486,539; 4,751,177; 5,210,015; 5,487, 972; 5,804,375; 5,994,076). Nucleic acid hybridization techniques and conditions are known to the skilled artisan and have been described for example, in Sambrook et al. *Molecular Cloning A Laboratory Manual,* 2nd Ed, Cold Spring Lab. Press, Dec. 1989: U.S. Pat. Nos. 4,563,419 (Raaki) and 4,851,330 (Kohne) and in Dunn, et al., *Cell* 12, pp. 23-26 (1978) among many other publications.

Earlier molecular methods developed to detect and identify MRSA based on the detection of the mecA gene and *S. aureus*-specific chromosomal sequences have been described. (Saito et al, 1995, *J. Clin. Microbiol* 33:2498-2500; Ubukata et al., 1992, *J. Clin, Microbiol* 30:1728-1733; Murakami et al., 199, *J. Clin. Microbiol,* 29:2240-2244; Hiramatsu et al., 1992, *Microbiol Immunol,* 36:445-453). However, in tests based on the detection of the cassette junction only, false positives have been observed with methicillin-susceptible *S. aureus* isolates containing a small fragment of the right extremity of the SCCmec (see Rupp, J. et al., *J. Clin. Microbiol*, 44(6): 2317 (2006)). Additionally, Ramakrishnan and Riccelli describe a method for detecting MRSA utilizing oligonucleotide probes having sequences that are complementary to regions near the left junction of the SCCmec cassette insertion site, including part of the SCCmec cassette sequence and part of the *S. aureus* sequence in the region of insertion (the left extremity junction region) (U.S. patent publication No. U.S. 20060057613).

Concepts for determining resistance to methicillin carried specifically by *S. aureus* have been published:
- the SCCmec right extremity junction amplification concept (Hiramatsu et al. WO97/31125; EP 0 887 424; U.S. Pat. No. 6,156,507; and further, Huletsky and Rossbach WO02/099034 (2002); Huletsky et al., *J. Clin. Microbiol* 42(5): 1875-1884 (2004))
- the immuno-enrichment concept described by Francois and co-workers (Francois, P et al. *J. Clin. Microbiol.* 41(1):254-260 (2003); WO02082086), in which the immuno-enrichment is followed by amplification of three markers (mecA gene, *S. aureus*-specific marker, and *S. epidermidis*-specific marker)
- the combination of SCCmec right extremity junction amplification and mecA amplification (Jay, et al. U.S. 20090203013; WO2009085221, which are incorporated by reference in their entirety).

The SCCmec right extremity junction concept is based on the amplification of a region covering the right extremity junction region of the SCCmec integration site. The principle is the following: the SCCmec cassette always integrates the *S. aureus* chromosome upstream of a *S. aureus* specific open reading frame called orfX; the amplification (e.g., PCR) assay combines multiple forward primers located on the right part of the cassette ("right extremity junction region" of SCCmec cassette), one reverse primer and a probe, both located in the *S. aureus* chromosomal orfX, i.e., downstream of the right extremity junction of SCCmec with orfX ("right extremity junction region" of orfX). Hiramatsu et al., describe a test with two forward primers in the right extremity junction region of the cassette to amplify the main SCCmec types described at that time (one primer for SCCmec types I and II and a second primer for type III). Huletsky et al set forth that several MRSA strains were not detected if only the two forward primers described by Hiramatsu were used, and they determined new types of cassettes named as MREJ types having sequence variations in the right part of the SCCmec cassette. A commercially available (Infectio Diagnostics Inc.) test combines five forward primers located in the right part of the cassette (one primer was designed for the detection of MREJ types i and ii and the four others for the MREJ types iii, iv, v and vii), one reverse primer located in the orfX, and three generic probes covering the same portion of the orfX region and required to identify the orfX variants identified. This test is performed in real-time PCR, However, the specificity of this test as reported (Huletsky et al. 2004) shows that 4.6% of MSSA (26 out of 569 tested) were misidentified. False-positive result has also been reported with another commercial test using a single-locus (right extremity SOCmec cassette-orfX junction) PCR assay (Rupp et al. *J. Clin. Microbiol* (44)6:2317 (2006)).

U.S. 20090203013 addressed primary sources of MRSA false positives and provided an improved test to detect MRSA that had not been previously addressed by then-available tests. This application provided that the identification of false positives by the previous molecular methods can be explained in some instances by the presence in MSSA strains of a residual SCOmec right extremity fragment following the deletion of a chromosomal region containing mecA or the presence of an SCCmec which does not contain mecA. Additionally, it provided that some portion, of the false positives can be due to non specific amplification; indeed, because the reverse primer and the probes are located in the orfX which is common to both MRSA and MSSA, non specific annealing of the forward primer(s) on MSSA chromosome will lead to amplification and detection of MSSA. The application addressed both sources of False positives and provided an improved test. An assay utilizing this principle is marketed (NucliSENS EasyQ® MRSA, bioMérieux, S A, Marcy l'Etoile, France).

Previously, in assays for detection of methicillin resistance in *S. aureus*, either the mecA gene was determined to be present in the SCCmec cassette leading the strain to be resistant to methicillin or the mecA gene was determined to be absent (excision from, the cassette or no cassette) wherein it was concluded that the strain was susceptible to methicillin. Taking into account the numerous sequences available in public databanks for mecA gene, from MRSA or from, other methicillin-resistance pathogens, the mecA gene was shown as well-conserved, only some particular mutations were found.

Recently a methicillin-resistant *S. aureus* was detected that was found to lack mecA by conventional PCR and microarray sequencing (Shore et al., *Araimicrob. Agents Chemother*. Doi:10.1128/AAC.00187-11 (Jun. 2, 2011) and Garcia-Alvarez, L. et al, Lancet doi:10.1016/S1473-3099 (11)70126-8 (Jun. 3, 2011) Methicillin-resistant *Staphylococcus aureus* with a novel mecA homologue in human and bovine population in the UK and Denmark: a descriptive study.). Whole-genome sequencing; revealed a 30 kb SCCmec element having a highly divergent blaZ-mecA-mecRI-mecI, and indicated that the mec element present in the SCCmec element had 70% sequence identity to *S. aureus* mecA homologues; further, the SCCmec element was almost identical to SCCmec type XI previously identified (sequence type 425 bovine MRSA strain LGA251 listed on the website of the International Working Group on the Classification of Staphylococcal Cassette Chromosome Elements). The SCCmec element is integrated at the same nucleotide position within orfX as all other SCCmec elements. The strain additionally included a class E mec complex a type 8 cassette chromosome recombinase (ccr) complex consisting of ccr/Al-ccrB3, an arsenic resistance operon and flanking direct repeats. Present detection methods would not identify this strain as MRSA.

Shore et al. used the FR823292 strain as reference strain and used mecA_M10/0061 primers. Garcia-Alvarez et al studied a divergent mecA in the LGA251 genome, this mecA variant being located in a novel cassette designated "type-XI SCCmec." They used the LGA251 strain as reference strain and used mecA_LGA251 primers. In fact, the 2publications refer to the same subject. Both mecA variants shared a very high similarity percentage (99%) and in the same time show a weak overall similarity to all mecA sequences known so far.

As new subtypes and strains are identified, means to detect such subtypes and strains becomes necessary. This is particularly important when a currently existing assay does not fortuitously already detect it and thus can result in false negative results. The present invention fills this need regarding detection of strains containing variant mecA by providing an assay that can detect such strains. Further, this new invention confirms in the same assay the presence of both a S. aureus strain; and a methicillin-resistance gene. This assay can be used alone or in combination with existing assays for other SCCmec types.

SUMMARY OF THE INVENTION

The present invention provides a method of amplifying in a sample a methiclliin-resistant Staphylococcus aureus (MRSA) which comprises an insertion of an SCCmec cassette within Staphylococcus aureus chromosomal DNA, wherein the SCCmec cassette comprises a mecA variant element, the method comprising:
  performing on the sample an amplification reaction, utilizing an oligonucleotide set comprising:
    a. a first oligonucleotide having a nucleic acid sequence capable of specifically hybridizing to a region of chromosomal Staphylococcus aureus DNA in an extremity junction region, and
    b. a second oligonucleotide having a nucleic acid sequence capable of specifically hybridizing to a region of a mecA variant,
  wherein each of the first oligonucleotide and the second oligonucleotide is oriented such that, under amplification conditions, if the sample contains the MRSA, the region of the MRSA between the hybridizing region of the first oligonucleotide and the hybridizing region of the second oligonucleotide is amplified.

The present invention, additionally provides a method of amplifying in a sample a methicillin-resistant Staphylococcus aureus (MRSA) which comprises an insertion of an SCCmec cassette within Staphylococcus aureus chromosomal DNA, wherein the SCCmec cassette comprises mecA or a mecA variant element, the method comprising:
  performing on the sample an amplification reaction utilizing
    a. a first oligonucleotide set comprising:
      1) a first mecA variant oligonucleotide having a nucleic acid sequence capable of specifically hybridizing to a first region of a mecA variant element, and
      2) a second mecA variant oligonucleotide having a nucleic acid sequence capable of specifically hybridizing to a second region of a mecA variant element: and
    b. a second oligonucleotide set comprising:
      1) a first mecA oligonucleotide having a nucleic acid sequence capable of specifically hybridizing to a first region of mecA, and
      2) a second mecA oligonucleotide having a nucleic acid sequence capable of specifically hybridizing to a second region of mecA
  wherein each of the first oligonucleotide and the second oligonucleotide is oriented such that, under amplification conditions, if the sample contains the MRSA, the region of the MRSA between the hybridizing region of the first oligonucleotide and the hybridizing region of the second oligonucleotide is amplified.

The present invention further provides a kit for amplifying a methicillin-resistant Staphylococcus aureus (MRSA) which comprises an insertion of an SCCmec cassette within Staphylococcus aureus chromosomal DNA, wherein the SCCmec cassette comprises a mecA variant element, the kit comprising a first oligonucleotide set comprising:
    a. a first oligonucleotide having a nucleic acid sequence capable of specifically hybridizing to a region of chromosomal Staphylococcus aureus DNA in an extremity junction region, and
    b. a second oligonucleotide having a nucleic acid sequence capable of specifically hybridizing to a region of a mecA variant.

Additionally, the present invention provides a kit for amplifying in a sample a methicillin-resistant Staphylococcus aureus (MRSA) which comprises an insertion of an SCCmec cassette within Staphylococcus aureus chromosomal DNA, wherein the SCCmec cassette comprises mecA or a mecA variant element, the kit comprising:
  a) a first oligonucleotide set comprising:
    1) a first mecA variant oligonucleotide having a nucleic acid sequence capable of specifically hybridizing to a first region of a mecA variant element, and
    2) a second mecA variant oligonucleotide having a nucleic acid sequence capable of specifically hybridizing to a second region of a mecA variant element; and
  b) a second oligonucleotide set comprising:
    1) a first mecA oligonucleotide having a nucleic acid sequence capable of specifically hybridizing to a first region of mecA, and
    2) a second mecA oligonucleotide having a nucleic acid sequence capable of specifically hybridizing to a second region of mecA.

DETAILED DESCRIPTION OF THE INVENTION

As discussed herein, the present invention provides the identification of strains of methicillin-resistant S. aureus which include a variant mecA gene (typically not detected with presently commercially-available MRSA detection kits) and which are structurally arranged such that a single amplification reaction can amplify both a relevant portion of mecA and an extremity junction at the insertion point, of a SCCmec cassette into the S. aureus chromosome. The present invention addresses a newly-discovered source of false negative results and provides an improved test.

Unless defined otherwise, all technical and scientific terms used herein have the same meanings as commonly understood by one of skill in the art to which the disclosed invention belongs. Although any methods and materials similar or equivalent to those described herein can be used in the practice or testing of the present invention, the preferred methods, devices, and materials are as described.

As used herein and in the appended claims, the singular forms "a," "an," and "the" include plural reference unless the context clearly dictates otherwise.

The strains identified by the present invention, are methicillin-resistant, but they do not harbour the classical mecA gene known to be well-conserved so far. Methicillin resistance is conferred in this case by a new mecA variant gene. One documented mecA variant is referred to in publications variously as mecA$_{LGA251}$, mecA$_{M10/0061}$, mecA homologue, and mecA$_{new\ variant}$ (this variant has more recently been proposed to be renamed "mecC" [Ito et al. "Guidelines for Reporting Novel mecA Gene Homologues" *Agents Chemother*, doi:10.1128/AAC.01199-12]); however, other mecA variants may be detected with the present invention. As used in the specification and the claims, the term "mecA variant" will be used to refer to anymecA variant gene that confers methicillin resistance and can be detected by a claimed method, in particular, in an amplification reaction that, with a single primer set, amplifies a region that includes both a relevant portion of a mecA variant (i.e., sufficient to identify it as a mecA variant) and an extremity junction at the insertion point of a SCCmec cassette into the *S. aureus* chromosome. It is noted that, as amplification technologies are further developed, longer amplicons may become possible such that primer sets for detection of a mecA variant gene may be designed to hybridize farther from this target region comprising a relevant portion of a mecA variant gene and an extremity junction of SCCmec cassette.

Figure 1:
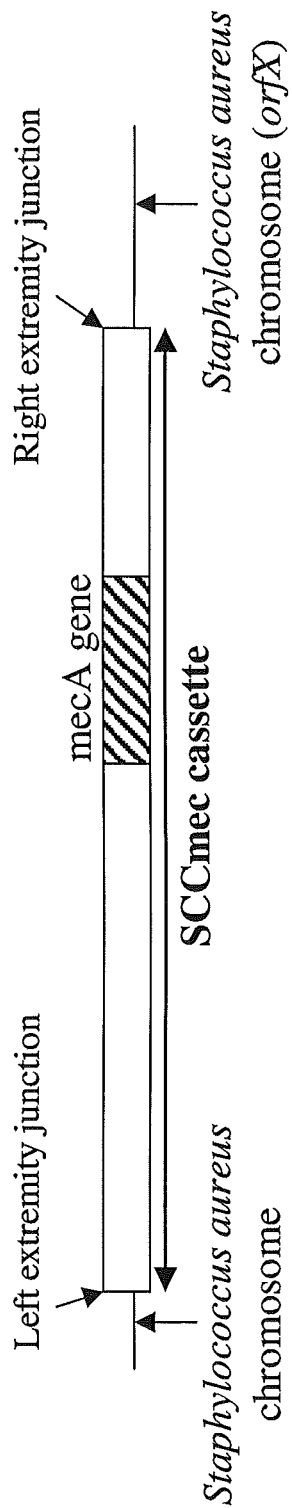
FIG. 1 shows the region of MRSA chromosome with the inserted SSCmec cassette, indicating the left and right extremity junctions.
Figure 2:
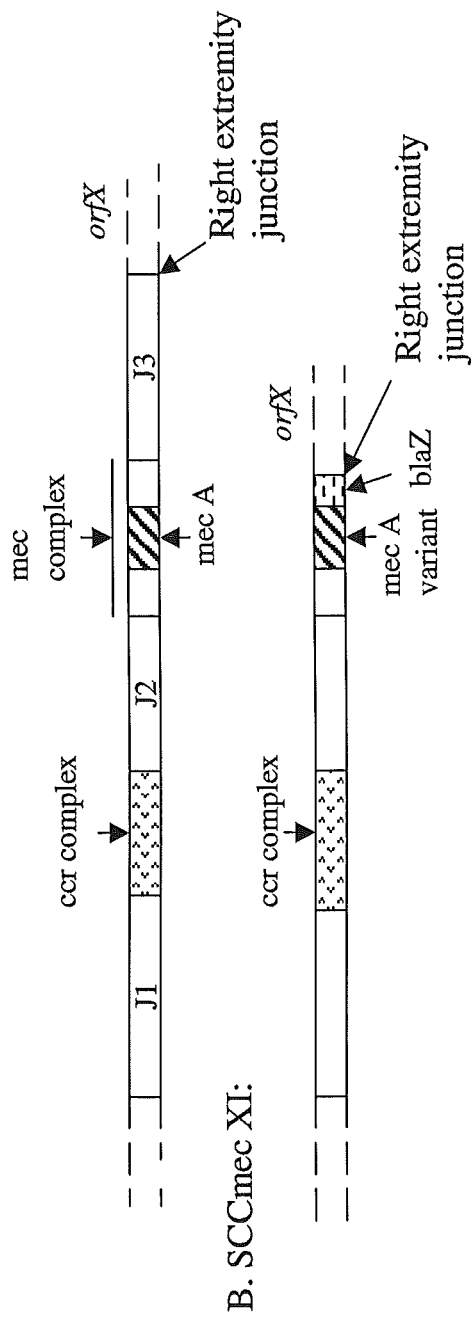
FIG. 2 shows the region of MRSA chromosome, with an inserted SCCmec cassette bearing a mecA variant (mecA$_{LGA251}$).

The size of the SCCmec cassettes in previously studied MRSA strains is divergent, but generally the mecA gene has been found to be about 8000 to 15,000 bp from the *S. aureus* chromosome in the direction of orfX (sometimes herein referred to as "downstream") and longer in the other direction (see FIG. 1 and FIG. 2a). In the new SCCmec type XI, the mecA variant gene has been found to be positioned closer to orfX, with the distance only about 1500 bp (see FIG. 2b). While application of traditional MRSA amplification designs might have predicted an assay design of two parts-detection of the mecA variant gene in addition to detection of the junction applicants instead considered and recognized the potential utility of the shorter distance from mecA variant gene to orfX. Thus, the present invention advantageously amplifies the region between the mecA variant gene and an *S. aureus* chromosomal extremity junction region (i.e., across an extremity junction) directly using a primer in the mecA variant gene and another in the *S. aureus* chromosome region in an extremity junction region (see FIG. 2, e.g., across the right extremity junction). While still an unconventionally long amplicon, applicants have found that this design works surprisingly well. Additionally, this new invention resolves the problem of poor specificity because only one amplification is needed and this amplification confirms in the same reaction the presence both of *S. aureus* strain and of variant methicillin-resistance gene.

The present invention provides a method of amplifying in a sample a methicillin-resistant *Staphylococcus aureus* (MRSA) which comprises an insertion of an SCCmec cassette within *Staphylococcus aureus* chromosomal DNA, wherein the SCCmec cassette comprises a mecA variant element, the method comprising:
performing on the sample an amplification reaction utilizing an oligonucleotide set comprising:
a. a first oligonucleotide having a nucleic acid sequence capable of specifically hybridizing to a region of chromosomal *Staphylococcus aureus* DNA in an extremity junction region, and
b. a second oligonucleotide having a nucleic acid sequence capable of specifically hybridizing to a region of a mecA variant,
wherein each of the first, oligonucleotide and the second oligonucleotide is oriented such that, under amplification conditions, if the sample contains the MRSA, the region of the MRSA between the hybridizing region of the first oligonucleotide and the hybridizing region of the second oligonucleotide is amplified. The region of chromosomal *S. aureus* DNA can be in a right extremity junction region.

Oligonucleotides of the present invention that specifically hybridize with a target can be selected as those which selectively hybridize, at the selected hybridization conditions, with their target, i.e., which bind with their intended target(s) but not with non-targets. Hybridization/amplification conditions can be selected for appropriate stringency to achieve selectivity, as is known in the art (e.g., Sambrook and Russell, *Molecular Cloning; A Laboratory Manual* (Cold Spring Harbor Laboratory Press; 3rd edition (2001)). Minor modifications can be made to select oligonucleotides as long as the reaction conditions allow the modified oligonucleotide to specifically hybridize to the target(s).

A first oligonucleotide having a nucleic acid sequence capable of specifically hybridizing to a region of chromosomal *Staphylococcus aureus* DNA in an extremity junction region and a second oligonucleotide having a nucleic acid sequence capable of specifically hybridizing to a region of a mecA variant each, can function as a primer, and each is oriented such that, upon hybridization, to its specific target nucleic acid, and upon initiation of an amplification reaction including the primer, an amplicon is formed that includes the region of the MRSA between the hybridizing region of the first oligonucleotide and the hybridizing region of the second oligonucleotide. Such a reaction is designed to amplify across an extremity junction of SCCmec at its insertion into the *S. aureus* chromosome (i.e., to be in sufficiently close proximity of the junction so that an amplification reaction can extend across the junction). Thus a primer pair for mecA variant useful for amplifying a junction will typically hybridize to two regions, one in the mecA variant and one in an *S. aureus* chromosomal region, in effect surrounding the junction, and each primer will be oriented to hybridize such as to be capable of directing amplification in a 5'-3' direction toward the junction. Typically, the primer for mecA variant would bedesigned to hybridize within 1600 nt, 1550 nt, 1500 nt. 1450 nt, 1400 nt, 1350 nt, 1300 nt, 1200 nt, 1100 m, 1000 nt, 900 nt, 800 nt, 700 nt, 600 nt, 500 nt, 400 nt, 350 nt, 3000 nt, 250 nt, 200 nt, 150 nt, 100 nt, 50 nt, 30 nt, 25 nt, 20 nt, etc. of the junction; however, as new technologies allow longer amplicons, primers can be designed that hybridize farther distances from the junction. The primer having a nucleic acid sequence capable of specifically hybridizing to a region of a mecA variant will typically be designed to hybridize farther from the junction than the primer having a nucleic acid sequence capable of specifically hybridizing to a region of chromosomal *Staphylococcus aureus* DNA in an extremity junction region because of the organization of the SCCmec having a mecA variant gene and the distance of the mecA variant gene from the junction.

The oligonucleotide set for amplification of orfX-mecA variant can further comprise a third oligonucleotide capable of specifically hybridizing within a region of the MRSA between the hybridizing region of the first oligonucleotide and the hybridizing region of the second oligonucleotide, and, wherein if the sample contains the MRSA, hybridization of the third oligonucleotide is detected. Such an oligonucleotide can function as a probe for detecting an amplification product and is therefore selected to be capable of specifically hybridizing to a region between the hybridizing region of the first oligonucleotide and the hybridizing, region of the second oligonucleotide. In certain embodiments, such a probe can specifically hybridize to a region of chromosomal *Staphylococcus aureus* DNA, such as a region of orfX. In another embodiment, a probe can specifically hybridize to a region of a right extremity junction region of SCCmec cassette DNA (e.g., within blaZ sequences), and in a further embodiment, a probe can specifically hybridize to a region of the mecA variant. Amplification can be detected by any means selected. For example, this third oligonucleotide can be labeled by any of several means and with any of several methods. Thus, if the sample contains the MRSA, amplification of the nucleic acid between the two primers occurs, and the third oligonucleotide, which can be a labeled probe, can hybridize to the amplicon. Hybridization of the third oligonucleotide can be detected by any known means. Alternatively, an intercalating dye can be used to detect amplification from the two primers. If a probe is used, the probe can be designed to specifically hybridize to a region of a right extremity junction region of SCCmec cassette DNA. For example, the probe can be designed to specifically hybridize to a region, of chromosomal *Staphylococcus aureus* DNA such as a region orfX of chromosomal *Staphylococcus aureus* DNA. Alternatively, a probe can be designed to specifically hybridize to a region of the mecA variant.

The presence or absence of any target within the present invention can be determined by performing whatever analysis provides detection of the product, e.g., if a labeled probe is used, detection of the hybridized label by the appropriate detection device. In such an embodiment, lack of a detectable signal indicates the absence of the target; perception of a detectable signal indicates presence of the target.

Examples of a first oligonucleotide, or primer, capable of specifically hybridizing to a region of chromosomal *Staphylococcus aureus* DNA in an extremity junction region can include, but are not limited to, an oligonucleotide that specifically hybridizes in the orfX region. Examples of such an oligonucleotide include SEQ ID NOS: 9 and 10. Examples of a second oligonucleotide having a nucleic acid sequence capable of specifically hybridizing to a region of a mecA variant can include, but are not limited to, a nucleic acid sequence selected from the group consisting of: SEQ ID NOS: 6, 7, 16, 17 and 21. These specific examples are particularly useful as forward primers (i.e., for directing amplification toward the right extremity junction of SCCmec). Examples of a third, oligonucleotide, which can be used as a probe, capable of specifically hybridizing within a region of the MRSA between the hybridizing region of the first oligonucleotide (hybridizing within in chromosomal *Staphylococcus aureus* DNA) and the hybridizing region of the second oligonucleotide (hybridizing within a region of a mecA variant) can include, but is not limited to, a nucleic acid sequence set forth as SEQ ID NO: 8, 18 and 19.

The genomic structure of MRSA has been characterized previously. As used in the claims, the "SCCmec cassette" (sometimes referred to as "mecDNA," e.g., in Hiramatsw U.S. Pat. No. 6,156,507) has the definition as known in the art, i.e., an integrated adventitious DNA existing on a chromosome of MRSA or MR-CNS and including the mec gene complex, a set of site-specific recombinase genes (ccrA and ccrB), and terminal inverted and direct repeats (at both 3' and 5' ends); as used in the specification, this term includes any variation of SCCmec found in strains harboring a mecA variant. "mecA gene" includes all sequences necessary to confer methicillin resistance (i.e., to encode PBP2a or PBP2' (Penicillin Binding Protein)).

As known in the art, insertion of the SCCmec cassette into the *S. aureus* chromosome creates two junctions, and two corresponding junction regions, of SCCmec DNA with *S. aureus* chromosomal DNA, wherein the SCCmec sequence is contiguous with the *S. aureus* chromosomal sequence. The junctions, therefore, are located at the left and right extremities of the SCCmec cassette (see FIG. 1). These two regions are named "Right SCCmec-Chromosome Junction" and "Chromosome-Left SCCmec junction" by Ito et al. (*Antimicrob. Agents Chemother*. May 2001 45(5): 1323-1336, "Structural Comparison of three Types of Staphylococcal Cassette Chromosome mec Integrated in the chromosome in Methicillin-Resistant *Staphylococcus aureus*"), and termed herein as "right extremity junction" and "left extremity junction," respectively. At the right extremity junction, the *S. aureus* genomic sequence abutting the SCCmec cassette, is the gene orfX, which is in some literature referred to as "IntM." As used in the claims, "extremity junction region" is a region of either SCCmec cassette or *S. aureus* chromosomal nucleic acid within distance of either the right or the left extremity junction, or insertion site, such that a primer that hybridizes in either SCCmec (e.g., J3 region) or orfX can, in a primer extension reaction or a transcription-type (e.g., NASBA or TMA) reaction, be extended across that junction, e.g., within 600 nt, 550 nt, 500 nt, 450 nt, 400 nt, 350 nt, 300 m, 250 nt, 200 m, 150 nt, 100 nt, or 50 nt (in either direction) of the junction. Useful distances may vary depending upon the amplification technology used. "Extremity junction region," therefore, depending upon context used, can refer to a region within the SCCmec DNA or a region within the *S. aureus* chromosomal DNA; both uses refer to such DNA within distance of the junction such that an appropriately selected primer that hybridizes in either SCCmec (e.g., J3 region) or orfX could, under appropriate, standard extension or amplification conditions, be extended, or transcribed, from it, in the direction of the junction, across the junction. That is, "an extremity junction region of the SCCmec cassette" would be a region within the SCCmec DNA near its abutment, or integration site, with the aureus chromosomal DNA; and "an extremity junction region of orfX" would be a region within the orfX DNA near an abutmentwith SCCmec DNA (an SCCmec integration site). Similarly, "an extremity junction region of chromosomal *S. aureus* DNA" would be a region within the chromosomal *S. aureus* DNA-near an abutment with SCCmec DNA. Alternatively, this region may also be referred to as chromosomal *S. aureus* DNA in the region of the SCCmec extremity junction. Thus, "right extremity junction region" refers to the region surrounding the junction on the right (or downstream) side of the SCCmec cassette, and "left extremity junction region" refers to the region surrounding the junction on the left (or upstream) side of the SCCmec cassette (see FIG. 1).

Advantageously, one can perform an amplification reaction to detect both the presence of previously characterized MRSA strains (containing the originally-described mecA gene), using known methods, such as one comprising detecting a SCCmec insertion junction and mecA sequences (i.e., Jay et al.), along with an amplification to detect the newly discovered strains harboring a mecA variant. Such an amplification and detection reaction can be performed, e.g., in separate containers or in a single container as a multiplex reaction. Thus, in addition to the reaction detecting a mecA variant, an assay can include a reaction to detect, e.g., a junction region of a standard (i.e., as described for SCCmec types I-X) SCCmec cassette insertion, a standard (i.e., as described for SCCmec types I-X)-mecA gene, and/or an *S. aureus*-specific chromosomal region.

By "amplifying a portion of mecA DNA" is meant performing an amplification reaction on a sample that produces an amplification product that includes sequences corresponding to any portion of a mecA gene, for example, the region between primers comprising a nucleic acid sequence set forth in SEQ ID NOS: 12 and 13. For example, a primer can comprise a nucleic acid sequence as set forth in SEQ ID NOS: 12 and 13. Primers comprising these sequences and primers consisting essentially of these sequences can be utilized as well as primers consisting of these sequences. Amplification can be detected, for example, utilizing a probe comprising a nucleic acid sequence between the target nucleic acids of the primers, or using an intercalating dye. Primers and probes can be readily designed for hybridization to the known mecA sequence.

Junction. The present inventive method, in addition to amplifying the mecA variant, if present, can further comprise amplifying a methicillin-resistant *Staphylococcus aureus* (MRSA) which comprises an insertion of an SCCmec cassette within *Staphylococcus aureus* chromosomal DNA, wherein the SCCmec cassette comprises a mecA, by utilizing in an amplification reaction a second oligonucleotide set for amplification of a right extremity junction of SCCmec cassette with *Staphylococcus aureus* chromosomal DNA, the second oligonucleotide set comprising:
   a. a first junction oligonucleotide having a nucleic acid sequence capable of specifically hybridizing within a region of chromosomal *Staphylococcus aureus* DNA in a right extremity junction region; and
   b. a second junction oligonucleotide having a nucleic acid sequence capable of specifically hybridizing within a region, of a right extremity junction region of the SCCmec cassette of the MRSA comprising a mecA,
   wherein each of the first junction oligonucleotide and the second junction oligonucleotide is oriented such that, under amplification conditions, if the sample contains the MRSA comprising a mecA, the right junction is amplified. The second oligonucleotide set can further comprise a third junction oligonucleotide having a nucleic acid sequence capable of specifically hybridizing within a region of the MRSA between the hybridizing region of the first junction oligonucleotide and the hybridizing region of the second junction oligonucleotide, wherein if the sample contains the MRSA comprising the right extremity junction, hybridization of the third junction oligonucleotide is detected.

The third junction oligonucleotide can be a probe. The third junction oligonucleotide can have a nucleic acid sequence capable of specifically hybridizing within a region of a right extremity junction region of the SCCmec cassette, or it can have a nucleic acid sequence capable of specifically hybridizing within orfX. Alternatively, a method of detection such as use of an intercalating dye can be performed. The first junction oligonucleotide, which can function as an amplification primer, can have a nucleic acid sequence capable of specifically hybridizing within orfX.

Primers and probes used in any reaction of this invention are capable of specifically hybridizing with a target nucleic acid. Specific hybridization is known in the art, and, typically, specific hybridization is achieved through nucleic acid identity or high similarity of the primer/probe with the target nucleic acid and/or through use of stringent hybridization conditions (e.g., stringent temperature and/or salt conditions). Specific hybridization provides selective hybridization to the target within the reaction.

Typically, for amplification reactions other than that to amplify orfX-mecA variant nucleic acids (such as to amplify a junction, a non-variant mecA and/or an *S. aureus* chromosomal region), the primer is selected such that amplification product synthesized utilizing if and a second primer (located in an *S. aureus* genomic sequence) will be of approximately 100 to 350 nt in length. While PCR amplification can be designed to generate longer or shorter amplicons (e.g., 50, 100, 150, 200, 250, 300, 350, 400, 500, 600, 700, 800, 900, 1000 nt or longer), preferred amplicon lengths for either transcription-based (e.g., NASRA or TMA) or PCR-type reactions for detection of mecA, junction or chromosomal *S. aureus* genes in the present invention will be within about 100 to 300 nt (e.g., 150, 200, 250, 300 nt) in length. Additionally, for a multiplex amplification reaction, whether transcription-based or PCR-based, an amplicon in the range of 100 to 300 nt or shorter is preferable for these targets, to enhance sensitivity of the test. It is noted that the amplification utilizing a first oligonucleotide having a nucleic acid sequence capable of specifically hybridizing to a region of chromosomal *Staphylococcus aureus* DNA in an extremity junction region and a second oligonucleotide having a nucleic acid sequence capable of specifically hybridizing to a region of a mecA variant will have a longer amplicon than that typically used in other amplifications that can form partof the present assay. It is also noted that, as amplification methods are further developed and refined, longer amplicons may become possible and eventually routine and are encompassed by the present invention.

A primer oriented such that, "under amplification conditions, the junction is amplified" includes a primer oriented such that, upon hybridization to its specific target nucleic acid, and upon initiation of an amplification reaction including the primer, an amplicon is formed that includes the junction. Such a reaction is designed to amplify across the junction (i.e., to be in sufficiently close proximity of the junction so that a typical amplification reaction would extend across the junction). Thus a primer pair useful for amplifying a junction will typically hybridize to two regions that surround the junction and each primer will be oriented to hybridize in a 5'-3' direction toward the junction. Typically, the primer would be designed to hybridize within 600 nt, 500 nt, 400 nt, 350 nt, 300 nt, 250 nt, 200 nt 150 nt, 100 nt, 50 nt, 30 nt, 25 nt, 20 nt, etc. of the junction. A probe for detecting an amplification product is therefore selected to be capable of specifically hybridizing within a region of a right extremity junction region of the SCCmec cassette between the target sequences of the primers. For example, the probe can hybridize within *S. aureus* genomic sequences (e.g., orfX, between the target sequence of the *S. aureus* probe and the junction) or within SCCmec (between the target sequence of the SCCmec primer and the junction) or across the junction. In certain embodiments, such a probe can specifically hybridize fully within or primarily within SCCmec cassette. In one embodiment, in which the probe specifically hybridizes primarily within SCCmec cassette, the region to which the probe hybridizes can additionally include the junction and, therefore, at least one, or two or three or a few nucleotides of orfX that abut the junction. Typically, the primer is selected such that amplification product synthesized utilizing it and a second primer (located in an *S. aureus* genomic sequence) will be of approximately 100 to 350 nt in length. While PCR amplification can be designed to generate longer amplicons (e.g., 150, 200, 250, 300, 350, 400, 500, 600, 700, 800, 900, 1000 nt or longer), preferred amplicon lengths for either transcription-based (e.g., NASBA or TMA) or PCR-type reactions for detection of mecA, junction or chromosomal *S. aureus* genes in the present invention will be within about 100 to 300 nt (e.g., 150, 200, 250, 300 nt) in length. Additionally, for a multiplex amplification reaction, whether transcription-based or PCR-based, an amplicon in the range of 100 to 300 nt or shorter is preferable for these targets, to enhance sensitivity of the test. Specific primers useful for amplifying extremity junction regions can readily be designed, given the teachings herein and knowledge and skill in the art.

As used in the claims, "amplification conditions" are those appropriate for a selected amplification reaction, as are known to those of skill in the art, such as are utilized in various amplification reactions. Such conditions can be optimized for a specific reaction, primers, etc, as also known by the skilled artisan. As is known, such amplification conditions include contact with the required reagents for the amplification, e.g., nucleotides and enzymes, as well as the appropriate selected temperature, salt and pH conditions, among other aspects. Furthermore, as used in the claims, a primer or probe may be a primer or probe set, i.e., multiple primers or probes. Such primer/probe sets can be utilized in a reaction in which more than one type or subtype of MRSA is desired to be amplified and/or detected, and wherein the nucleic acid sequence of the target MRSA region selected for hybridization of the primer and/or probe varies among types and/or subtypes, individual primers/probes can be designed for each type or subtype, as exemplified herein.

mecA. The present method can additionally comprise amplifying a *Staphylococcus aureus* comprising mecA by utilizing in an amplification reaction a third oligonucleotide set for amplification of a mecA element comprising:
  a. a first mecA oligonucleotide having a nucleic acid sequence capable of specifically hybridizing within a region of mecA; and
  b. a second mecA oligonucleotide having a nucleic-acid sequence capable of specifically hybridizing within a second region within mecA, wherein each of the first mecA oligonucleotide and the second mecA oligonucleotide is oriented such that, under amplification conditions, a portion of the mecA is amplified. The third oligonucleotide set can further comprise a third mecA oligonucleotide having a nucleic acid sequence capable of specifically hybridizing within a region of the mecA between the hybridizing region of the first mecA oligonucleotide and the hybridizing region of the second mecA oligonucleotide wherein if the sample contains the MRSA comprising mecA, hybridization of the third mecA oligonucleotide is detected. Alternatively, a method of detection such as use of an intercalating dye can be used. Examples of primers for mecA can include SEQ ID NOS: 12 and 13.

By amplifying a portion of mecA DNA is meant performing an amplification reaction on a sample that produces an amplification product that includes sequences corresponding to any identifying portion of a mecA gene, for example, the region between primers comprising a nucleic acid sequence set forth in SEQ ID NOS: 12 and 13. Amplification can be detected using a probe that hybridizes between the target nucleic acids of the primers or using an intercalating dye. Primers and probes can be readily designed for hybridization to the known mecA sequence.

*S. aureus* chromosome. The present method can further comprise utilizing a fourth oligonucleotide set for amplification of a *Staphylococcus aureus*-specific chromosomal DNA comprising:
  a. a first aureus oligonucleotide having a nucleic acid sequence capable of specifically hybridizing within a region within *Staphylococcus aureus*-specific chromosomal DNA; and
  b. a second *S. aureus* oligonucleotide having a nucleic acid sequence capable of specifically hybridizing within a second region within *Staphylococcus aureus*-specific chromosomal DNA, wherein each of the firsts aureus oligonucleotide and the second *S. aureus* oligonucleotide is oriented such that, under amplification conditions, a portion of the *S. aureus*-specific DMA is amplified. The fourth oligonucleotide set can further comprise a third *S. aureus* oligonucleotide having a nucleic acid sequence capable of specifically hybridizing within a region of the *S. aureus* DNA between, the hybridizing region of the first *S. aureus* oligonucleotide and the hybridizing region of the second *S. aureus* oligonucleotide, wherein if the sample contains the region of the *S. aureus* DNA between the hybridizing region of the first *S. aureus* oligonucleotide and the hybridizing region of the second *S. aureus* oligonucleotide, hybridization of the third oligonucleotide is detected. Such third *S. aureus* oligonucleotide can function as a probe. The *Staphylococcus aureus*-specific chromosomal DNA can be any known *S. aureus*-specific genomic region, such as within the genes spa, orfX or nuc. Examples of primers for spa can include SEQ ID NOS: 24 and 25, and probe, SEQ ID NO:26. Examples of primers for orfX can include SEQ ID NOS: 9 and 10, and probe, SEQ ID NO: 11. Examples of primers for nuc can include SEQ ID NOS: 27, 28 and 30, and probe, SEQ ID NO:29. Alternatively, a method of detection, such as use of an intercalating dye can be performed.

The present invention comprises a method of amplifying in a sample a methicillin-resistant *Staphylococcus aureus* (MRSA) which comprises an insertion of an SCCmec cassette within *Staphylococcus aureus* chromosomal DNA, wherein the SCCmec cassette comprises mecA or a mecA variant element, the method comprising performing on the sample an amplification reaction utilizing
  a. a first oligonucleotide set comprising:
    1) a first mecA variant oligonucleotide having a nucleic acid sequence capable of specifically hybridizing to a first region of a mecA variant element, and
    2) a second mecA variant oligonucleotide having a nucleic acid sequence capable of specifically hybridizing to a second region of a mecA variant element; and
  b. a second oligonucleotide set comprising:
    1) a first mecA oligonucleotide having a nucleic acid sequence capable of specifically hybridizing to a first region of mecA, and
    2) a second mecA oligonucleotide having a nucleic acid sequence capable of specifically hybridizing to a second region of mecA, wherein each of the first oligonucleotide and the second oligonucleotide is oriented such that, under amplification conditions, if the sample contains the MRSA, the region of the MRSA between the hybridizing region of the first oligonucleotide and the hybridizing region of the second oligonucleotide is amplified. The first oligonucleotide set can further comprise a third mecA variant oligonucleotide capable of specifically hybridizing within a region of the MRSA between the hybridizing region of the first mecA variant oligonucleotide and the hybridizing region of the second mecA variant oligonucleotide, and wherein if the sample contains the MRSA comprising a mecA variant element, hybridization of the third mecA variant oligonucleotide is detected. The second oligonucleotide set can further comprise a third mecA oligonucleotide capable of specifically hybridizing within a region of the MRSA between the hybridizing region of the first mecA oligonucleotide and the hybridizing region of the second mecA oligonucleotide, and wherein if the sample contains the MRSA comprising mecA, hybridization of the third mecA oligonucleotide is detected. Such third oligonucleotide can be a probe. Alternatively, a method of detection such as use of an intercalating dye can be performed. By way of example, the first mecA variant oligonucleotide can comprise a nucleic acid sequence selected from the group consisting of SEQ ID NOS: 6, 7, 14, 15 and 20. The second mecA variant oligonucleotide can comprise a nucleic acid sequence selected from the group consisting of SEQ ID NOS: 5, 6, 17 and 21. The third mecA variant oligonucleotide can comprise a nucleic acid sequence selected from the group consisting of SEQ ID NOS: 8, 18 and 19. In such a method, the mecA variant can be mecA$_{LGA251}$ or it can be another mecA variant.

Junction. The method of amplifying in a sample a methicillin-resistant *Staphylococcus aureus* (MRSA) which comprises an insertion of an SCCmec cassette within *Staphylococcus aureus* chromosomal DNA, wherein the SCCmec cassette comprises mecA or a mecA variant element, can further comprise amplification of additional MRSA and/or *S. aureus* elements. For example, the method can comprise amplifying a methicillin-resistant *Staphylococcus aureus* (MRSA) which comprises an insertion of an SCCmec cassette within *Staphylococcus aureus* chromosomal DNA, wherein the SCCmec cassette comprises a mecA, by utilizing in an amplification reaction a second oligonucleotide set for amplification of a right extremity junction of SCCmec cassette with *Staphylococcus aureus* chromosomal DNA, the second oligonucleotide set comprising:
  a. a first junction, oligonucleotide having a nucleic acid sequence capable of specifically hybridizing within a region of chromosomal *Staphylococcus aureus* DNA in a right extremity junction region; and
  b. a second junction oligonucleotide having a nucleic acid sequence capable of specifically hybridizing within a region of a right, extremity junction region of the SCCmec cassette of the MRSA comprising a mecA,
wherein each of the first junction oligonucleotide and the second junction oligonucleotide is oriented such that under amplification conditions, if the sample, contains the MRSA comprising a mecA, the right junction is amplified. The third oligonucleotide set can further comprise a third junction oligonucleotide having a nucleic acid sequence capable of specifically hybridizing within a region of the MRSA between the hybridizing region of the first junction oligonucleotide and the hybridizing region of the second junction oligonucleotide, wherein if the sample contains the MRSA comprising the right extremity junction, hybridization, of the third junction oligonucleotide is detected. The third junction oligonucleotide can have a nucleic acid sequence capable of specifically hybridizing within a region of a right extremity junction region of the SCCmec cassette. The first junction oligonucleotide can have a nucleic acid sequence capable of specifically hybridizing within orfX. The third junction oligonucleotide can have a nucleic acid sequence capable of specifically hybridizing within orfX. Alternatively, a method of detection such as use of an intercalating dye can be performed.

*S. aureus.* The method of amplifying in a sample a methicillin-resistant *Staphylococcus aureus* (MRSA) which comprises an insertion of an SCCmec cassette within *Staphylococcus aureus* chromosomal DNA, wherein the SCCmec cassette comprises mecA or a mecA variant element, can further comprise utilizing a fourth oligonucleotide set for amplification of a *Staphylococcus aureus*-specific chromosomal DNA comprising:
  a. a first *S. aureus* oligonucleotide having a nucleic acid sequence capable of specifically hybridizing within a region within *Staphylococcus aureus*-specific chromosomal DNA; and
  b. a second *S. aureus* oligonucleotide having a nucleic acid sequence capable of specifically hybridizing within a second region within *Staphylococcus aureus*-specific-chromosomal DNA, wherein each of the first *S. aureus* oligonucleotide and the second *S. aureus* oligonucleotide is oriented such that, under amplification conditions, a portion of the *S. aureus*-specific DNA is amplified. The fourth oligonucleotide set can further comprise a third *S. aureus* oligonucleotide having a nucleic acid sequence capable of specifically hybridizing within, a region of the *S. aureus* DNA between the hybridizing region of the first *S. aureus* oligonucleotide and the hybridizing region of the second *S. aureus* oligonucleotide, wherein if the sample contains the region of the *S. aureus* DNA between the hybridizing region of the first *S. aureus* oligonucleotide and the hybridizing; region of the second *S. aureus* oligonucleotide, hybridization of the third oligonucleotide is detected. Such third *S. aureus* oligonucleotide can function as a probe. Alternatively, a method of detection such as use of an intercalating dye can be performed. The *Staphylococcus aureus*-specific chromosomal DNA can be selected from, for example, spa, orfX and nuc; however, other *S. aureus*-specific chromosomal DNA targets, as may be known to those of skill in the art, may be used.

It is to be recognized that, in addition to the amplification reaction detecting the presence of mecA variant, the invention includes that one can additionally amplify one or more additional relevant sequences, such as the SCCmec junction for SCCmec types other than those bearing mecA variant, mecA (non-variant), and an *S. aureus*-specific chromosomal sequence. One can combine any or all of these additional amplification reactions, in a multiplex reaction or in individual reactions.

A multiplex amplification reaction means that the specific reagents for amplification of more than one target are contacted together, such that more than one amplification can occur within the same reaction container. Additionally, detection reagents for more than one target can be included. Thus one can conduct a multiplex amplification and detection reaction by placing into contact all of the specific reagents for amplification and detection of more than one target.

Thus, in a multiplex reaction, one can amplify multiple target regions in the same reaction. Multiple amplification reactions can also be run sequentially. Simultaneous amplification can also be utilized, if a multiplex is not desired or feasible, wherein individual reactions are allowed to proceed at the same time, but the reagents for more than one amplification reaction are not necessarily all within the same reaction container or tube, but rather are earned out in separate reaction containers. It is understood that, even in a multiplex amplification reaction, each reaction will occur at whatever pace the individual reactions proceed under the provided conditions.

Detection can also be "simultaneous," meaning that, if appropriate probes for each reaction in the reaction container are included, under the appropriate conditions, detection of more than one target can be achieved in either a single reaction container (multiplex) or in more than one reaction container (appropriate probes distributed to the relevant reaction container). Such detection can be performed, if desired, in the same reaction container as the multiplex or simultaneous amplification reaction, and, further, can be performed while amplification reactions continue (i.e., real-time). In the single container can be included all components of a reaction mixture, tailored, to the specific amplification and detection method utilized. Thus, a "reaction mixture" can include all the necessary reagents for performing a reaction, which may include, but not be limited to, buffering agents to maintain pH at a selected level during a reaction, salts, co-factors, scavengers, and the like.

As used in the claims, "amplification conditions" are those appropriate for a selected amplification reaction, as are known to those of skill in the art, such as are utilized in various amplification reactions. Such conditions can be optimized for a specific reaction, primers, etc, as also known by the skilled artisan. As is known, such amplification conditions include contact with the required reagents for the amplification, e.g., nucleotides and enzymes, as well as the appropriate selected temperature, salt and pH conditions, among other aspects. Furthermore, as used in the claims, a primer or probe may be a primer or probe set, i.e., multiple primers or probes. Such primer/probe sets can be utilized in a reaction in which more than one type or subtype of MRSA is desired to be amplified and/or detected, and wherein the nucleic acid sequence of the target MRSA region selected for hybridization of the primer and/or probe varies among types and/or subtypes. Individual primers/probes can be designed for each type or subtype, as exemplified herein.

As used herein, an oligonucleotide "having" a nucleic acid sequence included in a portion of target DNA means the sequence has sufficient identity to the target DNA sequence, or its complement, to specifically and selectively hybridize to that target DNA under stringent hybridization conditions. It includes nucleic acid sequences having full sequence identity to the sequence.

Generally, amplification reactions producing amplicons (the product of a polynucleotide amplification reaction) are "template-driven" in that base pairing of reagents, either nucleotides or oligonucleotides, have complements in a template polynucleotide that are required for the creation of reaction products. In one aspect, template-driven reactions are primer extensions with a nucleic acid polymerase or oligonucleotide ligations with, a nucleic acid ligase. Amplification can include any known or newly designed method of amplification, including those used in published methods (e.g., transcription-based amplification such as transcription-mediated amplification (TMA) and nucleic acid sequence-based amplification NASBA (as exemplified herein), and cycling nucleic acid amplification technologies (thermocycling) such as polymerase chain reaction (PCR), reverse transcriptase PCR (RT-PCR), and ligase chain reaction (LCR), and any method of amplification, e.g., sustained sequence replication (3SR), strand displacement amplification (SDA), branched DNA (bDNA), cycling probe technology (CPT), solid phase amplification (SPA), rolling circle amplification technology (RCA), solid phase RCA, anchored SDA and nuclease dependent signal amplification (NDSA), all of which are known to the skilled artisan. An amplification reaction may be a "real-time" amplification if a detection chemistry is available that permits a reaction product to be measured as the amplification reaction progresses, e.g. real-time PCR or real-time NASBA. Thus this invention includes the use of any nucleic acid amplification method or any other procedure which may be used to increase the sensitivity and/or the rapidity of nucleic acid-based diagnostic tests. The present invention also includes the use of any detection technology including post-amplification detection technologies, any amplification technology combined with detection, any hybridization nucleic acid chips or array technologies, and any amplification chips or combination of amplification and hybridization chip technologies. Detection and identification by any nucleotide sequencing method is also within the present invention.

A variety of detection methods can be utilized in this invention. Detection methods utilizing nucleic acid probes are well known in the art. Probes of the present kits and/or for use in the present methods can be labeled by any selected label suitable for the detection method chosen, many of which are known in the art, such as a phosphatase (e.g., alkaline phosphatase), biotin, avidin, a peroxidase (e.g., horseradish peroxidase), digoxigenin, a fluorescent dye (such as Cy3 and Cy5 dyes, fluorescein, FAM, ROX), a chemiluminescent label, a chromophoric label, a radioactive label (e.g., a radioisotope) and a ligand. Probe designs for different detection methods can be used, such as target-capture, HPA, TaqMan, molecular beacons, scorpions and sandwich hybridization. Hybridization conditions can be selected in accordance with the type of probe and the type of detection reaction selected. Additionally, intercalating dyes can be utilized. An intercalating dye is one that binds specifically to double-stranded DNA fluoresce brightly upon such binding; in the absence of double stranded DNA, with nothing to bind to they only fluoresce at a low level. Detection is monitored by measuring the increase in fluorescence throughout the amplification cycle. An intercalating dye can, if desired, be used with melt analysis, as is known in the art. Examples of intercalating dyes can include, but are not limited to, ethidium bromide, SYBRY GREEN, LCGREEN, LCGREEN PLUS, RESOLIGHT, EVAGREEN and CHROMOFY and SYTO 9. Others will be known to those of skill in the art and new such dyes may become available.

The present method further provides useful kits for use in such amplification and detection methods. Specifically, the present invention provides a kit for amplifying a methicillin-resistant *Staphylococcus aureus* (MRSA) which comprises an insertion of an SCCmec cassette within *Staphylococcus aureus* chromosomal DNA, wherein the SCCmec cassette comprises a mecA variant element, the kit comprising a first oligonucleotide set comprising:

a. a first oligonucleotide, having a nucleic acid sequence capable of specifically hybridizing to a region of chromosomal *Staphylococcus aureus* DNA in an extremity junction region, and b. a second oligonucleotide having a nucleic acid sequence capable of specifically hybridizing to a region of a mecA variant. Such kit can further comprise a third oligonucleotide capable of specifically hybridizing within a region of the MRSA between the hybridizing region of the first oligonucleotide and the hybridizing region of the second oligonucleotide. Such third oligonucotide can be a probe. In a preferred embodiment, the first oligonucleotide comprises a nucleic acid sequence selected from the group consisting of SEQ ID NOS: 9 and 10. Also in a preferred embodiment, the second oligonucleotide comprises a nucleic acid sequence selected from the group consisting of: SEQ ID NOS: 6, 7, 14, 15, 16, 17, 20 and 21. Further, in another preferred embodiment, the third oligonucleotide comprises a nucleic acid sequence set forth as SEQ ID NOS: 8, 11, 18 and 19. The mecA variant for which this kit is useful to detect can be mecA$_{LGA251}$ or another mecA variant.

A kit of the present invention, for amplifying a methicillin-resistant *Staphylococcus aureus* (MRSA) which comprises an insertion of an SCCmec cassette within *Staphylococcus aureus* chromosomal DNA, wherein the SCCmec cassette comprises a mecA variant element, can further comprise one or more additional elements, including oligonucleotide sets for detection of additional MRSA and MSSA elements. Though sometimes described herein as "second," "third" or "fourth" oligonucleotide sets, choice of an additional nucleotide set is independent of the other options. For example, the kit can include oligonucleotide sets for amplification of one or more of the SCCmec junction for SCCmec types other than those bearing mecA variant, mecA (non-variant), and a *S. aureus*-chromosomal sequence. In one example, a kit can comprise a second oligonucleotide set comprising:
 a. a first junction, oligonucleotide having a nucleic acid sequence capable of specifically hybridizing within a region of chromosomal *Staphylococcus aureus* DNA in a right extremity junction region; and
 b. a second junction oligonucleotide having a nucleic acid sequence capable of specifically hybridizing within a region of a right extremity junction region of the SCCmec cassette. In another example, the kit can comprise a third oligonucleotide set for amplification of a mecA element comprising:
 a. a first mecA oligonucleotide having a nucleic acid sequence capable of specifically hybridizing within a region of mecA DNA: and
 b. a second mecA oligonucleotide having a nucleic acid sequence capable of specifically hybridizing within a second region within mecA DNA. Another example provides that the kit can comprise a fourth oligonucleotide set for amplification of a *Staphylococcus aureus* specific chromosomal DNA comprising:
 a. a first *S. aureus* oligonucleotide having a nucleic acid sequence capable of specifically hybridizing within a region within *Staphylococcus aureus*-specific chromosomal DNA; and
 b. a second *S. aureus* oligonucleotide having a nucleic acid sequence capable of specifically hybridizing within a second region within *Staphylococcus aureus*-specific chromosomal DNA.

Another kit of the present invention provides a kit for amplifying in a sample a methicillin-resistant *Staphylococcus aureus* (MRSA) which comprises an insertion of an SCCmec cassette within *Staphylococcus aureus* chromosomal DNA, wherein the SCCmec cassette comprises mecA or a mecA variant element, wherein the SCCmec cassette comprises mecA or a mecA variant element.
 a) a first oligonucleotide set comprising:
  1) a first mecA variant oligonucleotide having a nucleic acid sequence capable of specifically hybridizing to a first region of a mecA variant element, and
  2) a second mecA variant oligonucleotide having a nucleic acid sequence capable of specifically hybridizing to a second region of a mecA variant element; and
 b) a second oligonucleotide set comprising:
  1) a first mecA oligonucleotide having a nucleic acid sequence capable of specifically hybridizing to a first region of mecA, and
  2) a second mecA oligonucleotide having a nucleic acid sequence capable of specifically hybridizing to a second region of mecA. The kit can further comprise in the first oligonucleotide set a third mecA variant oligonucleotide capable of specifically hybridizing within a region of the MRSA between the hybridizing region of the first oligonucleotide and the hybridizing region of the second oligonucleotide. It can comprise in the second oligonucleotide set a third mecA oligonucleotide capable of specifically hybridizing within a region of the MRSA between the hybridizing region of the first oligonucleotide and the hybridizing region of the second oligonucleotide. In a specific example, the first mecA variant oligonucleotide can comprise a nucleic acid sequence selected from the group consisting of SEQ ID NOS: 9 and 10. In another example, the second mecA variant oligonucleotide comprises a nucleic acid sequence selected from the group consisting of SEQ ID NOS: 6, 7,14,15, 16, 17, 20 and 21. In another embodiment, in the first oligonucleotide set, the third mecA variant oligonucleotide comprises a nucleic acid sequence set forth as SEQ ID NOS: 8, 18 and 19. In any such kit, the mecA variant can preferably be mecA$_{LGA251}$; however, it can be another mecA variant.

A kit of this invention can further comprise a third oligonucleotide set comprising: a. a first junction oligonucleotide having a nucleic acid sequence capable of specifically hybridizing within a region of chromosomal *Staphylococcus aureus* DNA in a right extremity junction region; and b. a second junction oligonucleotide having a nucleic acid sequence capable of specifically hybridizing within a region of a right extremity junction region of the SCCmec cassette comprising mecA, wherein each of the first junction oligonucleotide and the second junction oligonucleotide is oriented such that, under amplification conditions in the presence of the MRSA wherein the SCCmec cassette comprises mecA, an SCCmec cassette right insertion junction is amplified. The third oligonucleotide set can further comprise a third junction oligonucleotide having a nucleic acid sequence capable of specifically hybridizing within a region of the MRSA between the hybridizing region of the first junction oligonucleotide and the hybridizing region of the second junction oligonucleotide.

A kit of this invention can further comprise a fourth oligonucleotide set comprising:
 a. a first *S. aureus* oligonucleotide having a nucleic-acid sequence capable, of specifically hybridizing within a region within *Staphylococcus aureus* specific chromosomal DNA; and
 b. a second *S. aureus* oligonucleotide having a nucleic acid sequence capable of specifically hybridizing within a second region within *Staphylococcus aureus*-specific chromosomal DNA, wherein each of the first *S. aureus* oligonucleotide and the second *S. aureus* oligonucleotide is oriented such that, under amplification conditions in the presence of an MRSA, a portion of *S. aureus*-specific DNA is amplified. The fourth oligonucleotide set can further comprise a third *S. aureus* oligonucleotide having a nucleic acid sequence capable of specifically hybridizing within a region of the *S. aureus* DNA between the hybridizing region of the first *S. aureus* oligonucleotide and the hybridizing region of the second *S. aureus* oilgonucleotide Probes of this invention, including those included in such kits, can advantageously be labeled for detection, as known by persons of skill in the art. Labels can appropriately be selected for the specific design and type of amplification reaction to be performed. Primer and probe reagents can be provided in any of several states, including dried, lyophilized, pelleted, spray-dried, or in liquid.

Kits of this invention can include additional elements, such as reagents for a selected amplification method (e.g., amplification enzyme(s), buffer(s), and/or restriction enzyme(s), among others), controls), reaction container(s), and the like. If an intercalating dye is to be used, such can be included in the kit. Additionally, a kit of the present invention can comprise a container comprising a kit as described herein. Elements can be provided in a single container or in more than one container. Such kits can be useful for performing multiplex amplifications.

It is noted that references to primer and probe sequences that include thymidine can be readily adapted to utilize uridine in substitution for thymidine, where useful for the particular assay. Furthermore, nucleotides may be modified by addition of chemical groups, or substitution of individual residues by analogues (e.g., 2'-O-methoxy versions). Additional such modified nucleotides are known in the art; some examples include hydroxymethyl nucleotides, methylated nucleotides, fluorinated nucleotides, alpha thio phosphate nucleotides, amine-modified nucleotides, methoxy nucleotides, carboxymethyl nucleotides, thio nucleotides, inosine, dihydrouridine, pseudouridine, wybutosine, queuosine, C7dGTP. Additional modified nucleotides are found in U.S. Pat. Nos. 5,405,950 and 5,633,364 (both, Mock and Lovern). Furthermore, a probe can comprise DNA, RNA, modified DNA or RNA, PNA, other synthetic nucleic acids or nucleic acid substitutes that use nucleotide bases as means of selectively hybridizing to a target.

The present method can be utilized on any selected sample, such as a direct patient sample, e.g., nasal or inguinal swab, perineum swab, axilla swab, throat swab, rectal swab, samples from wounds, all particularly suitable for screening, as well as particularly suitable for diagnosis, bronchoalveolar lavage or blood (e.g., septicemia or blood culture). Such samples typically contain a mixed population of organisms. Additionally, if desired, this method can be applied to a sample having only a single bacterial species or strain, e.g., samples utilizing isolation, culture, capture, and/or enrichment of MRSA.

The present invention is exemplified in the following examples. As taught throughout the specification, detection of mecA variant can be combined in any desired combination, in multiplex or multiple simplex form, with another desired assay, such as primers and/or probe(s) for mecA, genomic *S. aureus* and/or SCCmec junction.

EXAMPLES

Amplification Conditions

Amplifications using PCR can be performed tinder standard conditions. Such conditions can include:

MIX preparation (reaction performed in 25 µL):

| Reagent | Initial concentration | Final Concentration | for 1 sample (volume in µL) |
| --- | --- | --- | --- |
| Water | NA | NA | 16.15 |
| Buffer pH 8.6 (KCL 50 mM) | 50X | 1X | 0.50 |
| MgCl2 solution | 1M | 5.4 mM | 0.14 |
| Dntp | 10 mM | 0.124 mM | 0.31 |
| KCl | 1.2M | 14.8 mM | 0.31 |
| Forward Primer | 20 µM | 0.2 µM | 0.25 |
| Reverse Primer | 20 µM | 0.2 µM | 0.25 |
| Probe | 20 µM | 0.1 µM | 0.13 |
| BSA | 10 µg/µL | 0.5 µg/µL | 1.25 |
| Fast Start enzyme | 5 U/µL | 0.112 U/µL (3.6 U/rxn) | 0.72 |
| Target (µl) | NA | NA | 5 |

Amplification cycle on Biorad CFX96

| | Enzyme activation | Denaturation | Annealing/ Extending (optic on) |
| --- | --- | --- | --- |
| Temperature (° C.) | 95 | 95 | 65 |
| Time (sec) | 300 | 5 | 30 |
| Cycle(s) | 1 | 50 | |

Oligonucleotide Design

Oligonucleotides dedicated to amplification or detection and belonging to genomic regions described herein can be utilized whatever the method used for their design. Among these methods which can be used are, for example (without being limited), design by hand (human expertise in oligonucleotide design) or design using computer means (scripts, programs, software) Eberhardt N L. A shell program for the design of PCR primers using genetics computer group (GCG) software (7.1) on VAX/VMS systems, *Biotechniques* 1992 Dec;13(6):9147); Miisuhashi M., Technical report: Part 1. Basic requirements for designing optimal oligonucleotide probe sequences. *J Clin Lab Anal* 1996; 10(5):277-84).

Example 1

Design of mecA Variant Primers and Probes

Experiments were designed to develop a PCR amplifying the *Staphylococcus aureus* orfX-mecA variant region. Initially, to design, primer(s) on the orfX side of the SCCmec junction, two primers and one probe were designed in the orfX region. A mecA variant-specific set of oligos (for $mecA_{LGA}251$, also described in literature as $mecA_{M10/0061}$, mecA homologue, and $mecA_{new\ variant}$) were also designed. As the mecA variant orientation was initially unknown, we designed mecA variant divergent primers in order to obtain a mecA variant –orfX amplicon. Further candidates on both ends of mecA variant gene have been designed to develop specific PCR of *Staphylococcus aureus*. The PCR assay selected for mecA variant amplification across the SCCmec junction should generate an amplicon about 1300 nt long. The PCR assay selected for detection of the mecA variant element itself may vary from this amplicon size; for example, it may produce a shorter amplicon.

A mecA variant reference sequence was found on NCB1 with the following accession number; FR823292 and utilized for initial primer design. A first step was to design mecA variant-specific oligos. As the mecA variant orientation was initially unknown, mecA variant divergent primers (both at 5' and 3' ends of the mecA variant gene) were designed in order to obtain a mecA variant –orfX amplicon.

Design on 5' End of mecA Variant Gene
Standard PCR conditions, as described above, were utilized, unless noted differently.
Primer Design
Many primers were designed (data not shown); two were selected based on thermodynamic characteristics:

TABLE 1

5' forward primer characteristics

|  | mecAv-orfX-1 (SEQ ID NO: 1) | mecAv-orfX-2 (SEQ ID NO: 2) |
|---|---|---|
| FR823292, 5' end position | 3613 | 3614 |
| Sequence (5'→3') | ATGAAGCAATATCAAAGGA | TGAAGCAATATCAAAGGAA |
| Oligo length | 19 nt | 19 nt |
| Tm | 59° C. | 60° C. |
| % GC | 31% | 31% |
| Hairpin formation nsk assessment (Intramolecular Folding workflow) | NO - Intra-molecular structure stable | NO - Intra-molecular structure stable |
| Primer Dimer risk assessment (Hybridization workflow) | NO Primer-dimer risk predicted | NO Primer-dimer risk predicted |

Probe Design
Many probes for the 5' end of mecA variant were designed (data not shown), and three were selected based on thermodynamic characteristics:

TABLE 2

5' probes characteristics

|  | mecAv-orfX-3 (SEQ ID NO: 3) | mecAv-orfX-4 (SEQ ID NO: 4) | mecAv-orfX-5 (SEQ ID NO: 5) |
|---|---|---|---|
| FR823292, 5' end position | 3657 | 3655 | 3653 |
| Sequence (5'→3') | ATAACTTGGTTATTCAAAGATGACGATATT | ACTTGGTTATTCAAAGATGACGATATTGA | TGGTTATTCAAAGATGACGATATTGAGA |
| Oligo length | 30 nt | 29 nt | 28 nt |
| TM (Apollo PCR default) | 69° C. | 68° C. | 67° C. |
| % GC | 26% | 31% | 32% |
| Hairpin formation risk assessment (intramolecular Folding workflow) | NO- Intra-molecular structure stable | NO- Intra-molecular structure stable | NO- Intra-molecular structure stable |
| Primer Dimer risk assessment (Hybridization workflow) | NO Primer-dimer risk predicted | NO Primer-dimer risk predicted | NO Primer-dimer risk predicte |

Design on 3' End of mecA Variant Gene

Many forward primers for 3'end of mecA variant gene were designed (data not shown), and two of them were selected based on thermodynamic characteristics;

TABLE 3 mecA variant 3; forward primers characteristics

|  | mecAv-orfX-6 (SEQ ID NO: 6) | mecAv-orfX-7 (SEQ ID NO: 7) |
|---|---|---|
| FR823292, 5' end position | 1877 | 1863 |
| Sequence (5'→3') | ATCCTAATATGTTAATGGCGA | ATGGCGATTAATGTTAAAGA |
| Oligo length | 21 nt | 20 nt |
| Tm (Apollo PCR default) | 62° C. | 61° C. |
| % GC | 33% | 30% |
| Hairpin formation risk assessment (Intramolecular Folding workflow) | NO- Intra-molecular structure stable | NO- Intra-molecular structure stable |
| Primer Dimer risk assessment (Hybridization workflow) | NO Primer-dimer risk predicted | NO Primer-dimer risk predicted |

Probe Design

Many probes for 3' end of mecA variant gene were designed (see Table 4; additional data not shown), and one was selected based on thermodynamic characteristics:

TABLE 4 mecA variant 3' probe characteristics

|  | mecAv-orfX-8 (SEQ ID NO: 8) |
|---|---|
| FR823292, 5' end position | 1826 |
| Sequence (5'→3') | TGGCCAGCTATAATGCTACTATATCTGGA |
| Oligo length | 29 nt |
| Tm (Apollo PCR default) | 71° C. |
| % GC | 41% |
| Hairpin formation risk assessment (Intramolecular Folding workflow) | NO- Intra- molecular structure stable |
| Primer Dimer risk assessment (Hybridization workflow) | NO Primer-dimer risk predicted |

Oligos Compatibility

Input parameters: Temperature: 63° C.; [Na+]: 0.05 M; [Mg2+]:0.005 M; Strand concentration; 0.00001 M

TABLE 5 mecA variant oligonucleotide compatibility; Free Energy Unit is Kcal/mol

| DG | MecA variant Primer mecAv-orfX-1 (SEQ ID NO: 1) | MecA variant Primer mecAv-orfX-2 (SEQ ID NO: 2) | MecA variant Probe mecAv-orfX-3 (SEQ ID NO: 3) | MecA variant Probe mecAv-orfX-4 (SEQ ID NO: 4) | MecA variant Probe mecAv-orfX-5 (SEQ ID NO: 5) | MecA variant Primer mecAv-orfX-6 (SEQ ID NO: 6) | MecA variant Primer mecAv-orfX-7 (SEQ ID NO: 7) | MecA variant Probe mecAv-orf-X-8 (SEQ ID NO: 8) |
|---|---|---|---|---|---|---|---|---|
| MecA variant Primer mecAv-orfX-1 | −1.09 | −1.56 | −1.56 | −1.56 | −1.56 | −1.4 | −1.4 | −0.8 |
| MecA variant Primer mecAv-orfX-2 | −1.56 | −1.09 | −1.56 | −1.56 | −1.56 | −1.6 | −1.4 | −0.64 |

TABLE 5-continued mecA variant oligonucleotide compatibility; Free Energy Unit is Kcal/mol

| DG | MecA variant Primer mecAv-orfX-1 (SEQ ID NO: 1) | MecA variant Primer mecAv-orfX-2 (SEQ ID NO: 2) | MecA variant Probe mecAv-orfX-3 (SEQ ID NO: 3) | MecA variant Probe mecAv-orfX-4 (SEQ ID NO: 4) | MecA variant Probe mecAv-orfX-5 (SEQ ID NO: 5) | MecA variant Primer mecAv-orfX-6 (SEQ ID NO: 6) | MecA variant Primer mecAv-orfX-7 (SEQ ID NO: 7) | MecA variant Probe mecAv-orfX-8 (SEQ ID NO: 8) |
|---|---|---|---|---|---|---|---|---|
| MecA variant Probe mecAv-orfX-3 | −1.56 | −1.56 | −1.09 | −1.56 | −1.56 | −1.4 | −1.4 | −1.04 |
| MecA variant Probe mecAv-orfX-4 | −1.56 | −1.56 | −1.56 | −1.09 | −1.56 | −1.4 | −1.4 | −1.04 |
| MecA variant Probe mecAv-orfX-5 | −1.56 | −1.56 | −1.56 | −1.56 | −1.09 | −1.4 | −1.4 | −1.04 |
| MecA variant Primer mecAv-orfX-6 | −1.4 | −1.6 | −1.4 | −1.4 | −1.4 | −0.77 | −1.24 | −1.77 |
| MecA variant Primer mecAv-orfX-7 | −1.4 | −1.4 | −1.4 | −1.4 | −1.4 | −1.24 | −0.77 | −1.77 |
| MecA variant Probe mecAv-orfX-8 | −0.8 | −0.64 | −1.04 | −1.04 | −1.04 | −1.77 | −1.77 | −2.88 |

All the above oligonucleotides were found to be compatible together and also compatible with oligonucleotides designed and selected in the orfX (see below). These experiments provided the orientation of mecA variant gene and conclude that oligos designed in 3′-end of mecA variant will be used for a mecA variant-orfX amplification reaction.

Example 2 mecA Variant-orfX Amplification Reaction

Standard PCR conditions, as described above, were utilized, unless noted differently.

Example 2a

Selection of Primers

Tests were performed on one mecA variant (+) strain (Internal collection strain number 11.56001) at 10 ng/μl, and one mecA(+) strains (ATCC 43300 strain) at 10 ng/μl. Primers tested were:
  orfX MRSA primers:
    mecAv-orfX-9 (SEQ ID NO:9): 10 μM
    mecAv-orfX-10 (SEQ ID NO:10): 10 μM
  mecA variant 3′-end primers:
    mecAv-orfX-6 (SEQ ID NO:6): 10 μM
    mecAv-orfX-7 (SEQ ID NO:7); 10 μM
  Conditions for all PCR reactions for primer selection were as follows:
    PCR format: 45 μl MIX+5 μl target
    PCR conditions; 4 conditions have been tested (see below)
    Expand High Fidelity PCR system (Roche, ref 11732650001, Lot Number 11398326)
    GeneAmp PCR system 9700

TABLE 6

PCR 4 tested conditions:

| Temperature | Time | Cycle |
|---|---|---|
| Table 6a: | | |
| Condition 1/thermo no20555 | | |
| 95° C. | 2 min | 1 cycle |
| 95° C. | 30 s | 30 cycles |
| 55° C. | 20 s | |
| 72° C. | 30 s | |
| 72° C. | 7 min | 1 cycle |
| 4° C. | infinite | 1 cycle |
| Table 6b: | | |
| Condition 2/thermo no20556 | | |
| 94° C. | 2 min | 1 cycle |
| 94° C. | 15 s | 30 cycles |
| 55° C. | 30 s | |
| 72° C. | 45 s | |
| 72° C. | 7 min | 1 cycle |
| 4° C. | infinite | 1 cycle |
| Table 6c: | | |
| Condition 3/thermo no20557 | | |
| 95° C. | 5 min | 1 cycle |
| 95° C. | 30 s | 35 cycles |
| 55° C. | 45 s | |
| 72° C. | 1 min | |
| 72° C. | 7 min | 1 cycle |
| 4° C. | infinite | 1 cycle |
| Table 6d: | | |
| Condition 4/thermo no20596 | | |
| 95° C. | 5 min | 1 cycle |
| 95° C. | 1 min | 35 cycles |
| 55° C. | 1′30 | |
| 72° C. | 2 min | |
| 72° C. | 7 min | 1 cycle |
| 4° C. | infinite | 1 cycle |

The following primers that selectively hybridize in mecA variant (mecA$_{LGA251}$) were tested in the listed specific conditions:

MIX 1: positive control for mecA variant
MIX 2: test oligo mecAv-orfX6 (SEQ ID NO:6) in mecA variant (amplicon 1498 nt long)
MIX 3: test oligo mecAv-orfX-7 (SEQ ID NO:7) in mecA variant (amplicon 1484 nt long)

TABLE 7a

Positive Control
MIX 1: Positive Control

| Reagent | MIX/tube | Final Concentration | 4 tubes |
|---|---|---|---|
| Buffer 10X | 5 µl | 1X | 20 µl |
| MgCl2 25 mM | 3 µl | 1.5 mM | 12 µl |
| dNTP 25 mM | 0.4 µl | 0.2 mM | 1.6 µl |
| Primer + Control 10 µM | 2 µl | 0.4 µM | 8 µl |
| Primer + Control 10 µM | 2 µl | 0.4 µM | 8 µl |
| Enzyme 3.5 U/µl | 0.74 µl | 2.6 U | 3 µl |
| H$_2$O acros qsp 45 µl | 31.86 µl | NA | 127.4 µl |
| Total MIX | 45 µl | | 180 µl |
| Target: DNA 10 ng/µl | 5 µl | 50 ng | |
| TOTAL | 50 µl | | |

TABLE 7b orfX- mecA variant Assay
MIX 2: mecAv-orfX-9/mecAv-orfX-10/mecAv-orfX-6

| Reagent | MIX/tube | Final Concentration | 10 tubes |
|---|---|---|---|
| Buffer 10X | 5 µl | 1X | 50 µl |
| MgCl2 25 mM | 8 µl | 4 mM | 80 µl |
| dNTP 25 mM | 1.2 µl | 0.6 mM | 12 µl |
| mecAv-orfX-9 10 µM | 3 µl | 0.6 µM | 30 µl |
| mecAv-orfX-10 10 µM | 3 µl | 0.6 µM | 30 µl |
| mecAv-orfX-6 10 µM | 3 µl | 0.6 µM | 30 µl |
| Enzyme 3.5 U/µl | 1 µl | 3.5 U | 10 µl |
| H$_2$O acros qsp 45 µl | 20.8 µl | NA | 208 µl* |
| Total MIX | 45 µl | | 450 µl |
| Target: DNA 10 ng/µl | 5 µl | 50 ng | |
| TOTAL | 50 µl | | |

TABLE 7c orfX- mecA variant Assay
MIX 3: mecAv-orfX-9/mecAv-orfX-10/mecAv-orfX-7

| Reagent | MIX/tube | Final Concentration | 10 tubes |
|---|---|---|---|
| Buffer 10X | 5 µl | 1X | 50 µl |
| MgCl2 25 mM | 8 µl | 4 mM | 80 µl |
| dNTP 25 mM | 1.2 µl | 0.6 mM | 12 µl |
| mecAv-orfX-9 10 µM | 3 µl | 0.6 µM | 30 µl |
| mecAv-orfX-10 10 µM | 3 µl | 0.6 µM | 30 µl |
| mecAv-orfX-7 10 µM | 3 µl | 0.6 µM | 30 µl |
| Enzyme 3.5 U/µl | 1 µl | 3.5 U | 10 µl |
| H$_2$O acros qsp 45 µl | 20.8 µl | NA | 208 µl* |
| Total MIX | 45 µl | | 450 µl |
| Target: DNA 10 ng/µl | 5 µl | 50 ng | |
| TOTAL | 50 µl | | |

Results/Conclusions of Assay:

TABLE 8

Results of orfX- mecA variant Assay:

| | Results | | | | |
|---|---|---|---|---|---|
| | mecA variant | orfX- mecA variant (mecAv-orfX-6) | | | |
| Sample ID | condition 1 | condition 1 | condition 2 | condition 3 | condition 4 |
| strain #1156001 from internal strain collection | + | + | + | + | + |
| ATCC 43300 strain | − | − | − | − | NA |
| H2O | − | − | − | − | NA |

| | Results | | | | |
|---|---|---|---|---|---|
| | mecA variant | orfX- mecA variant (mecAv-orfX-7) | | | |
| Sample ID | condition 1 | condition 1 | condition 2 | condition 3 | condition 4 |
| strain #1156001 from internal strain collection | + | + | + | + | + |
| ATCC 43300 strain | − | − | − | − | NA |
| H$_2$O | − | − | − | − | NA |

All conditions are found to be working; positive results were obtained for mecA variant and negative results were obtained for mecA. Both mecA variant primers were effective in amplifying the mecA variant-orfX amplicon and therefore for use in an assay to detect mecA variant-bearing MRSA strains. Details of an orfX-mecA variant PCR using orfX primer mecAv-orfX-9, mecA variant primer mecAv-orfX-7 and orfX primer mecAv-orfX-10 that was prepared and conducted is provided below. Successful amplification of the mecA variant (mecA$_{LGA251}$) was achieved.

TABLE 9

OrfX-mecA variant PCR:
MIX: PCR orfX-mecA variant

| Reagent | Initial [C] | Final Concentration | Vol/tube |
|---|---|---|---|
| Buffer | 10X | 1X | 5 µl |
| MgCl$_2$ | 25 mM | 4 mM | 8 µl |
| dNTP | 25 mM | 0.6 mM | 1.2 µl |
| mecAv-orfX-9 | 10 µM | 0.6 µM | 3 µl |
| mecAv-orfX-10 | 10 µM | 0.6 µM | 3 µl |
| mecAv-orfX-7 | 10 µM | 0.6 µM | 3 µl |
| Enzyme | 3.5 U/µl | 3.5 U | 1 µl |
| H$_2$O acros qsp 45 µl | NA | NA | 20.8 µl |
| Total MIX | | | 45 µl |
| DNA | 10 ng/µl | 50 ng | 5 µl |
| TOTAL | | | 50 µl |

Cycles PCR

| Temperature | Time | Cycle |
|---|---|---|
| 94° C. | 2 min | 1 cycle |
| 94° C. | 15 s | |
| 55° C. | 30 s | 30 cycles |
| 72° C. | 45 s | |
| 72° C. | 7 min | 1 cycle |
| 4° C. | infinite | 1 cycle |

Example 2b

Amplification with Probe in orfX and Probe in the mecA Variant Gene

Next, probe was added and the PCR was tested on Bio-Rad instrument (real time PCR system). Tests were done with TaqMan probe either in the orfX (mecAv-orfX-11 (SEQ ID NO: 11)) or in the mecA variant gene (mecA$_{LGA251}$:3' end) (mecAv-orfX-8 (SEQ ID NO:8)) (see below). The fluorophore used for both Taqman probes is FAM. DNA from five samples (10 ng/μl) was tested.

| Probe | SEQ ID NO | Sequence (5'→3') |
|---|---|---|
| mecAv-orfX-11 | 11 | TGATGCGGGTTGTGTTAATTGAGCAAGTG |
| mecAv-orfX-8 | 8 | TGGCCAGCTATAATGCTACTATATCTGGA |

Amplifications were performed under the following conditions;
PCR format: 45 μl MIX+5 μl target
PCR conditions: 2 probes were tested at 2 concentrations (0.3 μM and 0.6 μM)
Expand High Fidelity PCR system (Roche, ref 11732650001, lot number 11398326)
The following combinations of primers and probes (all, 10 μM) were utilized,
MIX 1: mecAv-orfX-9/mecAv-orfX-10/mecAv-orfX-7/mecAv-orfX-11 at 0.6 μM
MIX 2: mecAv-orfX-9/mecAv-orfX-10/mecAv-orfX-7/mecAv-orfX-11 at 0.3 μM
MIX 3: mecAv-orfX-9/mecAv-orfX-10/mecAv-orfX-7/mecAv-orfX-8 at 0.6 μM
MIX 4: mecAv-orfX-9/mecAv-orfX-10/mecAv-orfX-7/mecAv-orfX-8 at 0.3 μM
Results were as follows:

| Results | | MIX 1 mecAv-orfX-11/0.6 μM | | MIX 2 mecAv-orfX-11/0.3 μM | | MIX 3 mecAv-orfX-8/0.6 μM | | MIX 4 mecAv-orfX-8/0.3 μM | |
|---|---|---|---|---|---|---|---|---|---|
| Sample Id | Strains | Cq | End RFU | Cq | End RFU | Cq | End RFU | Cq | End RFU |
| 1 | mecAv (+) | 29.51 | 65.5 | 21.61 | 819 | 28.48 | 90.9 | 17.92 | 1331 |
| 2 | mecAv (+) | 25.89 | 70.3 | N/A | 32.5 | 25.8 | 57.7 | N/A | 1.41 |
| 3 | mecAv (+) | 29.53 | 47.7 | N/A | 38.1 | 20.37 | 91.3 | 26.56 | 124 |
| 4 | mecA (+) | N/A | 9.58 | 28.65 | 47.5 | N/A | −8.87 | N/A | 3.63 |
| 5 | MSSA | N/A | 6.52 | 30.32 | 53 | N/A | −1.35 | N/A | 0.746 |
| H$_2$O | NA | 6.37 | 172 | N/A | 1.36 | N/A | 3.26 | N/A | 0.0398 |
| | | | RFU: threshold with 40 | | | | | | |

The results indicate that ideal probe concentration, under these conditions, can be around 0.3 μM. Results with probe in orfX or in mecA variant gene both gave good-results. In general, under these conditions, the test seems to be more specific with probe in mecA variant gene; however, one can adjust the parameters, such as conducting the annealing step at 55° C., to optimize the assay. Further optimization can also be done, for example, one can increase the number of cycles, add a FAM read after the last step at 72° C., and/or increase the annealing temperature. This experiment shows that on MRSA strains, a specific real time PCR is feasible between the orfX and mecA variant gene despite very long amplicons generated (around 1484 bp).

Example 3

Amplification of SCCmec:orfX Junction Region of non-type XI and of mecA

An assay can be performed in combination with an assay for SCCmec typeXI to additionally detect the presence or absence of non-typeXI SCCmec-carrying MRSA strains (those that harbor mecA). An assay can also be performed in combination with an assay for other sequences, such as *S. aureus* genomic region(s) and/or mecA to additionally characterize the organism(s) present in a sample. These assays can be performed in multiplex or separately.

Example 3a

Detection of Right Extremity Junction Region

For detection of the right extremity junction in SCCmec types other than type XI, one can utilize, either in a multiplex with an assay to detect type XI or separately, primers located in the right part of the SCCmec cassette and in the orfX. This reaction can use probes located either in the right, part of the cassette or in the orfX, MRSA and MSSA strains can be tested using a lysate as target corresponding to 10$^5$ CFU per amplification reaction or as directed for a specific kit. For example, commercially available kits that can be utilized to detect this junction include:

| | |
|---|---|
| NucliSens EasyQ ® MRSA | BioMerieux (Marcy l'Etoile, France) |
| BD GeneOhm ™ MRSA Assay | Becton Dickinson (Franklin Lakes, NJ) |
| BD GeneOhm ™ MRSA ACP Assay | Becton Dickinson |
| BD MAX MRSA assay | Becton Dickinson |
| PLEX-ID MRSA assay | Abbott (Ibis Biosdences) (Abott Park, IL) |
| Detect-Ready ™ MRSA Assay | Molecular Detection Inc. (MDI) (Wayne, PA) |
| LightCycler ® MRSA Advanced Test | Roche (Pleasanton, CA) |
| Xpert MRSA | Cepheid (Sunnyvale, CA) |
| Xpert MRSA/SA BC | Cepheid |
| Xpert MRSA/SA SSTI | Cepheid |

Additionally, primers can be designed using Path-MRSA or Path-MRSA std (both, Genesig).

As shown in this example, simultaneous amplification and detection of both the insertion cassette region and the mecA gene can be utilized to reduce detection of certain Strains, (false MRSA positive) for non-type XI strains. As described and exemplified in Jay, etui. (U.S. 20090203013; WO2009085221, incorporated by reference) and available commercially (NucliSens EasyQ® MRSA (bioMerieux, Marcy I'Etoile, France)), this strategy can be used for a multiplex amplification for detection of both the mecA gene and the cassette junction region in the same tube. In one example, the assay uses 5 SCCmec cassette-specific forward primers in SCCmec right extremity junction region, 1 reverse primer in orfX, and 5 labeled SCCmec cassette-specific probes for the cassette junction region in combination with 1 forward primer, 1 reverse primer and 1 labeled probe for mecA. The results of such an assay show that, in the case of an MSSA possessing the insertion cassette region without the mecA gene, this portion of the assay can properly provide a "MRSA negative" result (SCCmec junction (+) plus mecA (−)).

Example 4

Amplification of MRSA Genomic Region (spa)

Standard PCR conditions, as described above, are utilized, unless noted differently.

The *S. aureus* spa gene is a gene encoding the protein A, which is a surface protein found specifically in the cell wall of *Staphylococcus aureus* bacteria. One part of spa gene, the polymorphic region X, is highly variable and is used for the spa typing permitting to differentiate several *S. aureus*. However more conservative areas are also present in spa gene and are used as specific markers to detect all the *S. aureus* strains. [Kuhn, J C M 2007, "Double-locus sequence typing using clfB and spa, a fast and simple method for epidemiological typing of methicillin-resistant Staphlococcus aureus"].

After building a multiple sequence alignment (from a collection of sequences from proprietary and/or public databanks), the oligonucleotides were designed in the conservative area of the gene. The resulting amplification and/or detection of the spa region demonstrate that *S. aureus* is present, in the sample.

Oligonucleotides are as follows;

| Oligo | SEQ ID NO | Sequence |
|---|---|---|
| S. aureus-1 Primer | 24 | CACCTGCTGCAAATGCTG (18 nt) |
| S. aureus-2 Primer | 25 | CGTTGATCAGCRTTTAAGTTAGGCATATT (29 nt) |
| S. aureus-3 Probe | 26 | CGCAACACGATGAAGCTCAACAAAATGC (28 nt) |

Example 5

Amplification of MRSA Genomic Region (nuc)

The nuc gene encodes the *S. aureus* thermostable nuclease also called thermonuclease. This gene is *S. aureus* specific and is highly conserved [Bragstad et al. J C M 1992, "Detection of *Staphylococcus aureus* by polymerase chain reaction amplification of the nuc gene"].

After building a multiple sequence alignment (from a collection of sequences from proprietary and/or public databanks), the oligonucleotides were designed in the conservative area of the gene. The resulting amplification and/or detection of the nuc region, under standard PCR conditions as described herein, demonstrates that *S. aureus* is present in the sample.

Oligonucleotides are as follows:

| Oligo | SEQ ID NO | Sequence |
|---|---|---|
| S. aureus-4 primer | 27 | GGTGTAGAGAAATATGGTCCTGAAGC (26 nt) |
| S. aureus-5 primer | 28 | GTCCTGAAGCAAGTGCATTTACG (23 nt) |
| S. aureus-6 Probe | 29 | GGACGTGGCTTAGCGTATATTTATGCTGATG (31 nt) |
| S. aureus-7 primer | 30 | GCAACTTTAGCCAAGCCTTGAC (22 nt) |

Example 6

Amplification of mecA and mecA Variant

Standard PCR conditions, as described above, can be utilized, unless noted differently.

mecA encodes PBP2a (Penicillin Binding Protein 2a), which is a modified PBP. mecA variant discovered recently also encodes for a protein belonging to the PBP2a family. After building a multiple sequence alignment (from a collection of sequences from proprietary and/or public databanks), the oligonucleotides were designed in conservative areas of the gene. Oligonucleotides can be designed in order to amplify and detect both, mecA and mecA variant either in the same simplex reaction or in several distinct simplex reactions or in multiplex reaction. The resulting amplification and/or detection of mecA and/or mecA variant (in simplex or multiplex) demonstrate that the methicillin resistance, gene is present in the sample.

mecA can be assayed by amplification using the following oligonucleotides, under standard PCR conditions;

| Oligo | SEQ ID NO | Sequence |
|---|---|---|
| Fwd Primer mecA-1 | 12 | ACCTTCTACACCTCCATATCAC (22 nt) |
| Rev Primer mecA-2 | 13 | CGTTACGGATTGCTTCACTG (20 nt) | mecA variant can be assayed by amplification using the following oligonucleotides to detect mecA variant sequences:

| Oligo | SEQ ID NO | Sequence |
|---|---|---|
| Fwd Primer mecAv-1 | 14 | AACACTGATGGTTTTAAGGTATCCA (25 nt) |
| Fwd Primer mecAv-2 | 15 | AAGGTATCCATTGCAAATACTTATGACAA (29 nt) |
| Rev Primer mecAv-3 | 16 | TACCAGATCCATCGTATTTTTCATATGT (29 nt) |

| Oligo | SEQ ID NO | Sequence |
|---|---|---|
| Rev Primer mecAv-4 | 17 | TACCAGATCCATCGTCATTTTTCATAT (27 nt) |
| Probe mecAv-5 | 18 | ATTGGAGAAAAAGGCTGAAAACGGAA (26 nt) |
| Probe mecAv-6 | 19 | ATTGGAGAAAAAGGCTGAAAACGGAAAAGA (30 nt) |
| Fwd Primer mecAv-7 | 20 | CCAGATATAGTAGCATTATA (20 nt) |
| Rev Primer Probe mecAv-8 | 21 | AAAGATGACGATATTGAG (18 nt) |

Alternatively, mecA variant can be determined using a mecA variant-orfX assay. One such assay is exemplified above in Example 2.

An assay to detect both mecA and mecA variant is described below. Primer/probe sequences are selected in a region common to both mecA and mecA variant.

mecA+mecA variant can be amplified using the following oligonucleotides;

| Oligo | SEQ ID NO | Sequence |
|---|---|---|
| Primer mecA-mecAv-1 | 22 | TCACCAGGTTCAACYCAAAA (20 nt) |
| Primer mecA-mecAV-2 | 23 | CCTGAATCWGCTAATAATATTTC (23 nt) |

All patents, patent publications and non-patent publications cited herein and the material for which they are cited are specifically incorporated by reference herein. Nothing herein is to be construed as an admission that the invention is not entitled to antedate such disclosure by virtue of prior invention.

It is understood that the disclosed invention is not limited to the particular methodology, protocols, and reagents described as these may vary. It is also to be understood that the terminology used herein is for the purpose of describing particular embodiments only, and is not intended to limit the scope of the present invention which will be limited only by the appended claims.

Those skilled in the art will recognize, or be able to ascertain using no more than routine experimentation, many equivalents to the specific embodiments of the invention described herein. Such equivalents are intended to be encompassed by the following claims.

SEQUENCES

| Oligonucleotide | SEQ ID NO | Target | Sequence |
|---|---|---|---|
| mecAv-orfX-1 | 1 | MecA variant-orfX | ATGAAGCAATATCAAAGGA (19 nt) |
| mecAv-orfX-2 | 2 | MecA variant-orfX | TGAAGCAATATCAAAGGAA (19 nt) |
| mecAv-orfX-3 | 3 | MecA variant-orfX | ATAACTTGGTTATTCAAAGATGACGATATT (30 nt) |
| mecAv-orfX-4 | 4 | MecA variant-orfX | ACTTGGTTATTCAAAGATGACGATATTGA (29 nt) |
| mecAv-orfX-5 | 5 | MecA variant-orfX | TGGTTATTCAAAGATGACGATATTGAGA (28 nt) |
| mecAv-orfX-6 | 6 | MecA variant-orfX | ATCCTAATATGTTAATGGCGA (21 nt) |
| mecAv-orfX-7 | 7 | MecA variant-orfX | ATGGCGATTAATGTTAAAGA (20 nt) |
| mecAv-orfX-8 | 8 | MecA variant-orfX | TGGCCAGCTATAATGCTACTATATCTGGA (29 nt) |
| mecAv-orfX-9 | 9 | MecA variant-orfX | TCAGCAAAATGACATTTCCACATCA (25 nt) |
| mecAv-orfX-10 | 10 | MecA variant-orfX | TCAGCAAAATGACATTCCCACATCA (25 nt) |
| mecAv-orfX-11 | 11 | MecA variant-orfX | TGATGCGGGTTGTGTTAATTGARCAAGTG (29 nt) |
| mecA-1 | 12 | mecA | ACCTTCTACACCTCCATATCAC (22 nt) |
| mecA-2 | 13 | mecA | CGTTACGGATTGCTTCACTG (20 nt) |
| mecAv-1 | 14 | mecA variant | AACACTGATGGTTTTAAGGTATCCA (25 nt) |
| mecAv-2 | 15 | mecA variant | AAGGTATCCATTGCAAATACTTATGACAA (29 nt) |

SEQUENCES

| Oligonucleotide | SEQ ID NO | Target | Sequence |
|---|---|---|---|
| mecAv-3 | 16 | mecA variant | TACCAGATCCATCGTCATTTTTCATATGT (29 nt) |
| mecAv-4 | 17 | mecA variant | TACCAGATCCATCGTCATTTTTCATAT (27 nt) |
| mecAv-5 | 18 | mecA variant | ATTGGAGAAAAGGCTGAAAACGGAA (26 nt) |
| mecAv-6 | 19 | mecA variant | ATTGGAGAAAAGGCTGAAAACGGAAAAGA (30 nt) |
| mecAv-7 | 20 | mecA variant | CCAGATATAGTAGCATTATA (20 nt) |
| mecAv-8 | 21 | mecA variant | AAAGATGACGATATTGAG (18 nt) |
| mecA-mecAv-1 | 22 | mecA + mecA variant | TCACCAGGTTCAACYCAAAA (20 nt) |
| mecA-mecAv-2 | 23 | mecA + mecA | CCTGAATCWGCTAATAATATTTC (23 nt) |
| S. aureus-1 | 24 | spa | CACCTGCTGCAAATGCTG (18 nt) |
| S. aureus-2 | 25 | spa | CGTTGATCAGCRTTTAAGTTAGGCATATT (29 nt) |
| S. aureus-3 | 26 | spa | CGCAACACGATGAAGCTCAACAAAATGC (28 nt) |
| S. aureus-4 | 27 | nuc | GGTGTAGAGAAATATGGTCCTGAAGC (26 nt) |
| S. aureus-5 | 28 | nuc | GTCCTGAAGCAAGTGCATTTACG (23 nt) |
| S. aureus-6 | 29 | nuc | GGACGTGGCTTAGCGTATATTTATGCTGATG (31 nt) |
| S. aureus-7 | 30 | nuc | GCAACTTTAGCCAAGCCTTGAC (22 nt) |

What is claimed is:

1. A kit for amplifying in a sample a methicillin-resistant *Staphylococcus aureus* (MRSA) which comprises an insertion of a SCCmec cassette within *Staphylococcus aureus* chromosomal DNA, wherein the SCCmec cassette comprises a mecA variant element, the kit consisting essentially of:
   a) a first oligonucleotide set consisting of:
      1) a first oligonucleotide having a nucleic acid sequence that specifically hybridizes to chromosomal *Staphylococcus aureus* DNA in an extremity junction region, and
      2) a second oligonucleotide having a nucleic acid sequence that specifically hybridizes to a mecA variant,
      wherein the first oligonucleotide and the second oligonucleotide each has a structure such that, under amplification conditions, the region of the MRSA between the hybridizing site of the first oligonucleotide and the hybridizing site of the second oligonucleotide is amplified as a single amplicon;
   b) optionally a pair of control primers;
   c) optionally a probe; and
   d) optionally one or more reagents.

2. The kit of claim 1, wherein the kit comprises the probe and the probe is at least one probe that is a third oligonucleotide that specifically hybridizes within a region of the MRSA between the hybridizing site of the first oligonucleotide and the hybridizing site of the second oligonucleotide.

3. The kit of claim 1, wherein the first oligonucleotide comprises a nucleic acid sequence selected from the group consisting of SEQ ID NO:9 and SEQ ID NO:10.

4. The kit of claim 1, wherein the second oligonucleotide comprises a nucleic acid sequence selected from the group consisting of SEQ ID NO:6, SEQ ID NO:7, SEQ ID NO:14, SEQ ID NO:15, SEQ ID NO:16, SEQ ID NO:17, SEQ ID NO:20 and SEQ ID NO:21.

5. The kit of claim 2, wherein the third oligonucleotide comprises a nucleic acid sequence selected from the group consisting of SEQ ID NO:8, SEQ ID NO:11, SEQ ID NO:18 and SEQ ID NO:19.

6. The kit of claim 1, wherein the mecA variant is mecA$_{LGA251}$.

7. A kit for amplifying in a sample a methicillin-resistant *Staphylococcus aureus* (MRSA) which comprises an insertion of a SCCmec cassette within *Staphylococcus aureus* chromosomal DNA, wherein the SCCmec cassette comprises a mecA variant element, the kit consisting essentially of:
   a) a first oligonucleotide set consisting of:
      1) a first oligonucleotide having a nucleic acid sequence that specifically hybridizes to chromosomal *Staphylococcus aureus* DNA in an extremity junction region, and
      2) a second oligonucleotide having a nucleic acid sequence that specifically hybridizes to a mecA variant,
      wherein the first oligonucleotide and the second oligonucleotide in the first oligonucleotide set each has a structure such that, under amplification conditions, the region of the MRSA between the hybridizing site of the first oligonucleotide and the hybridizing site of the second oligonucleotide is amplified as a single amplicon;
   b) a second oligonucleotide set comprising:
      1) a first junction oligonucleotide having a nucleic acid sequence that specifically hybridizes within chromosomal *Staphylococcus aureus* DNA in a right extremity junction region; and
      2) a second junction oligonucleotide having a nucleic acid sequence that specifically hybridizes within a right extremity junction region of the SCCmec cassette,
      wherein the first junction oligonucleotide and the second junction oligonucleotide each has a structure such that, under amplification conditions, the right extremity junction is amplified;
   c) optionally a pair of control primers;
   d) optionally a probe; and
   e) optionally one or more reagents.

8. A kit for amplifying in a sample a methicillin-resistant *Staphylococcus aureus* (MRSA) which comprises an insertion of a SCCmec cassette within *Staphylococcus aureus* chromosomal DNA, wherein the SCCmec cassette comprises a mecA variant element, the kit consisting essentially of:
   a) a first oligonucleotide set consisting of:
      1) a first oligonucleotide having a nucleic acid sequence that specifically hybridizes to chromosomal *Staphylococcus aureus* DNA in an extremity junction region, and
      2) a second oligonucleotide having a nucleic acid sequence that specifically hybridizes to a mecA variant,
      wherein the first oligonucleotide and the second oligonucleotide in the first oligonucleotide set each has a structure such that, under amplification conditions, the region of the MRSA between the hybridizing site of the first oligonucleotide and the hybridizing site of the second oligonucleotide is amplified as a single amplicon;
   b) a second oligonucleotide set for amplification of a mecA element consisting of:
      1) a first mecA oligonucleotide having a nucleic acid sequence that specifically hybridizes within mecA DNA; and
      2) a second mecA oligonucleotide having a nucleic acid sequence that specifically hybridizes within mecA DNA, wherein the first mecA oligonucleotide and the second mecA oligonucleotide each has a structure such that, under amplification conditions, a portion of the mecA DNA is amplified;
c) optionally a pair of control primers;
d) optionally a probe; and
e) optionally one or more reagents.

9. A kit for amplifying in a sample a methicillin-resistant *Staphylococcus aureus* (MRSA) which comprises an insertion of a SCCmec cassette within *Staphylococcus aureus* chromosomal DNA, wherein the SCCmec cassette comprises a tnecA variant element, the kit consisting essentially of:
a) a first oligonucleotide set consisting of:
1) a first oligonucleotide having a nucleic acid sequence that specifically hybridizes to chromosomal *Staphylococcus aureus* DNA in an extremity junction region, and
2) a second oligonucleotide having a nucleic acid sequence that specifically hybridizes to a mecA variant,
wherein the first oligonucleotide and the second oligonucleotide in the first oligonucleotide set each has a structure such that, under amplification conditions, the region of the MRSA between the hybridizing site of the first oligonucleotide and the hybridizing site of the second oligonucleotide is amplified as a single amplicon;
b) a second oligonucleotide set for amplification of a *Staphylococcus aureus* specific chromosomal DNA consisting of:
1) a first *S. aureus* oligonucleotide having a nucleic acid sequence that specifically hybridizes within *Staphylococcus aureus* specific chromosomal DNA; and
2) a second *S. aureus* oligonucleotide having a nucleic acid sequence that specifically hybridizes within *Staphylococcus aureus* specific chromosomal DNA,
wherein the first *S. aureus* oligonucleotide and the second *S. aureus* oligonucleotide each has a structure such that, under amplification conditions, a portion of the *S. aureus* specific DNA is amplified;
c) optionally a pair of control primers;
d) optionally a probe; and
e) optionally one or more reagents.

10. A kit for amplifying in a sample a methicillin-resistant *Staphylococcus aureus* (MRSA) which comprises an insertion of a SCCmec cassette within *Staphylococcus aureus* chromosomal DNA, wherein the SCCmec cassette comprises mecA or a mecA variant element, the kit consisting essentially of:
a) a first oligonucleotide set consisting of:
1) a first mecA variant oligonucleotide having a nucleic acid sequence that specifically hybridizes to a mecA variant element, and
2) a second mecA variant oligonucleotide having a nucleic acid sequence that specifically hybridizes to a mecA variant element,
wherein the first oligonucleotide and the second oligonucleotide in the first oligonucleotide set each has a structure such that, under amplification conditions the region of the MRSA between the hybridizing site of the first oligonucleotide and the hybridizing site of the second oligonucleotide is amplified;
b) a second oligonucleotide set consisting of:
1) a first mecA oligonucleotide having a nucleic acid sequence that specifically hybridizes to mecA, and
2) a second mecA oligonucleotide having a nucleic acid sequence that specifically hybridizes to mecA;
c) optionally a pair of control primers;
d) optionally a probe; and
e) optionally one or more reagents.

11. The kit of claim 10, wherein the kit comprises the probe and the probe is at least one probe that is a third mecA variant oligonucleotide that specifically hybridizes within a region of the MRSA between the hybridizing site of the first mecA variant oligonucleotide and the hybridizing site of the second mecA variant oligonucleotide.

12. The kit of claim 10, wherein the kit comprises the probe and the probe is at least one probe that is a third mecA oligonucleotide that specifically hybridizes within a region of the MRSA between the hybridizing site of the first mecA oligonucleotide and the hybridizing site of the second mecA oligonucleotide.

13. The kit of claim 10, wherein the first mecA variant oligonucleotide comprises a nucleic acid sequence selected from the group consisting of SEQ ID NO:9 and SEQ ID NO:10.

14. The kit of claim 10, wherein the second mecA variant oligonucleotide comprises a nucleic acid sequence selected from the group consisting of SEQ ID NO:6, SEQ ID NO:7, SEQ ID NO:14, SEQ ID NO:15, SEQ ID NO:16, SEQ ID NO:17, SEQ ID NO:20 and SEQ ID NO:21.

15. The kit of claim 11, wherein the third mecA variant oligonucleotide comprises a nucleic acid sequence selected from the group consisting of SEQ ID NO:8, SEQ ID NO:18 and SEQ ID NO:19.

16. The kit of claim 10, wherein the mecA variant is $mecA_{LGA251}$.

17. A kit for amplifying in a sample a methicillin-resistant *Staphylococcus aureus* (MRSA) which comprises an insertion of a SCCmec cassette within *Staphylococcus aureus* chromosomal DNA, wherein the SCCmec cassette comprises mecA or a mecA variant element, the kit consisting essentially of:
a) a first oligonucleotide set consisting of:
1) a first mecA variant oligonucleotide having a nucleic acid sequence that specifically hybridizes to a mecA variant element, and
2) a second mecA variant oligonucleotide having a nucleic acid sequence that specifically hybridizes to a mecA variant element,
wherein the first oligonucleotide and the second oligonucleotide in the first oligonucleotide set each has a structure such that, under amplification conditions the region of the MRSA between the hybridizing site of the first oligonucleotide and the hybridizing site of the second oligonucleotide is amplified;
b) a second oligonucleotide set consisting of:
1) a first mecA oligonucleotide having a nucleic acid sequence that specifically hybridizes to mecA, and
2) a second mecA oligonucleotide having a nucleic acid sequence that specifically hybridizes to mecA;
c) a third oligonucleotide set comprising:
1) a first junction oligonucleotide having a nucleic acid sequence that specifically hybridizes within chromosomal *Staphylococcus aureus* DNA in a right extremity junction region; and
2) a second junction oligonucleotide having a nucleic acid sequence that specifically hybridizes within a right extremity junction region of the SCCmec cassette comprising
wherein the first junction oligonucleotide and the second junction oligonucleotide each has a structure such that, under amplification conditions right extremity-junction is amplified;
d) optionally a pair of control primers;
e) optionally a probe; and
f) optionally one or more reagents.

18. The kit of claim 17, wherein the kit comprises the probe and the probe is at least one probe that is a third junction oligonucleotide having a nucleic acid sequence that specifically hybridizes within a region of the MRSA between the hybridizing site of the first junction oligonucleotide and the hybridizing site of the second junction oligonucleotide.

19. A kit for amplifying in a sample a methicillin-resistant *Staphylococcus aureus* (MRSA) which comprises an insertion of a SCCmec cassette within *Staphylococcus aureus* chromosomal DNA, wherein the SCCmec cassette comprises mecA or a mecA variant element, the kit consisting essentially of:
a) a first oligonucleotide set consisting of:
1) a first mecA variant oligonucleotide having a nucleic acid sequence that specifically hybridizes to a mecA variant element, and
2) a second mecA variant oligonucleotide having a nucleic acid sequence that specifically hybridizes to a mecA variant element,
wherein the first oligonucleotide and the second oligonucleotide in the first oligonucleotide set each has a structure such that, under amplification conditions the region of the MRSA between the hybridizing site of the first oligonucleotide and the hybridizing site of the second oligonucleotide is amplified;
b) a second oligonucleotide set consisting of:
1) a first mecA oligonucleotide having a nucleic acid sequence that specifically hybridizes to mecA, and
2) a second mecA oligonucleotide having a nucleic acid sequence that specifically hybridizes to mecA;
c) a third oligonucleotide set consisting of:
1) a first *S. aureus* oligonucleotide having a nucleic acid sequence that specifically hybridizes within *Staphylococcus aureus* specific chromosomal DNA; and
2) a second *S. aureus* oligonucleotide having a nucleic acid sequence that specifically hybridizes within *Staphylococcus aureus* specific chromosomal DNA,
wherein the first *S. aureus* oligonucleotide and the second *S. aureus* oligonucleotide each has a structure such that, under amplification conditions, a portion of *S. aureus* specific DNA is amplified;
d) optionally a pair of control primers;
e) optionally a probe; and
f) optionally one or more reagents.

20. The kit of claim 19, wherein the kit comprises the probe and the probe is at least one probe that is a third *S. aureus* oligonucleotide having a nucleic acid sequence that specifically hybridizes within the *S. aureus* DNA between the hybridizing site of the first *S. aureus* oligonucleotide and the hybridizing site of the second *S. aureus* oligonucleotide.

* * * * *

UNITED STATES PATENT AND TRADEMARK OFFICE
CERTIFICATE OF CORRECTION

PATENT NO. : 10,829,825 B2
APPLICATION NO. : 15/177973
DATED : November 10, 2020
INVENTOR(S) : Paillier et al.

Page 1 of 6

It is certified that error appears in the above-identified patent and that said Letters Patent is hereby corrected as shown below:

On the Title Page

(30) Foreign Application Priority Data: Please correct "11306776" to read -- 11306776.3 --

(57) Abstract: Please correct "detection: of" to read -- detection of --

(56) References Cited, OTHER PUBLICATIONS, Page 2, Column 2, Line 19: Please correct "PCT/EP2012/078856" to read -- PCT/EP2012/076856 --

In the Specification

Column 1, Line 17: Please correct "37 C.F.R, 0" to read -- 37 C.F.R. § --

Column 1, Line 18: Please correct "EPS-" to read -- EFS- --

Column 1, Line 50: Please correct "(β-lactam" to read -- β-lactam --

Column 2, Line 11: Please correct "Q617F2" to read -- Q6I7F2 --

Column 2, Line 36: Please correct "LOR" to read -- LCR --

Column 2, Line 39: Please correct "Q-B replicase" to read -- Q-β replicase --

Column 2, Line 45: Please correct "Canico" to read -- Carrico --

Column 2, Line 56: Please correct "Raaki" to read -- Ranki --

Column 2, Line 63: Please correct "199" to read -- 1991 --

Column 3, Line 60: Please correct "SOCmec" to read -- SCC*mec* --

Signed and Sealed this
Sixth Day of April, 2021

Drew Hirshfeld
*Performing the Functions and Duties of the
Under Secretary of Commerce for Intellectual Property and
Director of the United States Patent and Trademark Office*

CERTIFICATE OF CORRECTION (continued)
U.S. Pat. No. 10,829,825 B2

Column 4, Line 2: Please correct "SCOmec" to read -- SCC*mec* --

Column 4, Line 28: Please correct "*Araimicrob.*" to read -- *Antimicrob.* --

Column 4, Line 56: Please correct "2publications" to read -- 2 publications --

Column 7, Line 3: Please correct "anymecA" to read -- any *mecA* --

Column 9, Line 46: Please correct "Hiramatsw" to read -- Hiramatsu --

Column 10, Line 15: Please correct "300m, 250 nt 200 m," to read -- 300 nt, 250 nt, 200 nt, --

Column 10, Line 34: Please correct "DNA-near" to read -- DNA near --

Column 10, Line 56: Please correct "I-X)-mecA gene" to read -- I-X) *mecA* gene --

Column 11, Line 66: Please correct "NASRA" to read -- NASBA --

Column 22, Line 36: Please correct "Miisuhashi" to read -- Mitsuhashi --

Column 22, Line 49: Please correct "mecA$_{LGA}$251" to read -- *mecA$_{LGA251}$* --

Column 22, Line 61: Please correct "NCB1" to read -- NCBI --

Column 23, Line 23, Table 1: Please correct "Hairpin formation nsk" to read -- Hairpin formation risk --

Column 24, Line 60, Table 2: Please correct "No Primer-dimer risk predicte" to read -- No Primer-dimer risk predicted --

Column 27, Line 47: Please correct "11.56001" to read -- 1156001 --

Column 28, Line 34, Table 6: Please correct "no20555" to read -- n°20555 --

Column 28, Line 42, Table 6: Please correct "no20556" to read -- n°20556 --

Column 28, Line 50, Table 6: Please correct "no20557" to read -- n°20557 --

Column 28, Line 58, Table 6: Please correct "no20596" to read -- n°20596 --

Column 31, Line 33: Please correct "MIX 3;" to read -- MIX 3: --

Column 32, Lines 63-64: After "(both, Genesig)." Please insert -- Example 3b Multiplex Amplification and Detection of *mecA* Gene and Cassette Insertion (Junction) Region --

Column 33, Line 1: Please correct "Jay, etui." to read -- Jay, et al. --

CERTIFICATE OF CORRECTION (continued)
U.S. Pat. No. 10,829,825 B2

In the Claims

Column 47, Line 15, Claim 1: Please correct "SCCmec" to read -- SCC*mec* --

Column 47, Line 16, Claim 1: Please correct "SCCmec" to read -- SCC*mec* --

Column 47, Line 17, Claim 1: Please correct "mecA variant" to read -- *mecA variant* --

Column 47, Line 25, Claim 1: Please correct "mecA variant" to read -- *mecA variant* --

Column 47, Line 55, Claim 6: Please correct "mecA variant" to read -- *mecA variant* --

Column 47, Line 56, Claim 6: Please correct "mecA$_{LGA251}$" to read -- *mecA*$_{LGA251}$ --

Column 47, Line 59, Claim 7: Please correct "SCCmec" to read -- SCC*mec* --

Column 47, Line 60, Claim 7: Please correct "SCCmec" to read -- SCC*mec* --

Column 47, Line 61, Claim 7: Please correct "mecA variant" to read -- *mecA variant* --

Column 48, Line 13, Claim 7: Please correct "mecA variant" to read -- *mecA variant* --

Column 48, Line 30, Claim 7: Please correct "SCCmec" to read -- SCC*mec* --

Column 48, Line 41, Claim 8: Please correct "SCCmec" to read -- SCC*mec* --

Column 48, Line 42, Claim 8: Please correct "SCCmec" to read -- SCC*mec* --

Column 48, Line 43, Claim 8: Please correct "mecA variant" to read -- *mecA variant* --

Column 48, Line 51, Claim 8: Please correct "mecA variant" to read -- *mecA variant* --

Column 48, Line 61, Claim 8: Please correct "mecA" to read -- *mecA* --

Column 48, Line 62, Claim 8: Please correct "mecA" to read -- *mecA* --

Column 48, Line 63, Claim 8: Please correct "mecA" to read -- *mecA* --

Column 48, Line 65, Claim 8: Please correct "mecA" to read -- *mecA* --

Column 48, Line 66, Claim 8: Please correct "mecA" to read -- *mecA* --

Column 49, Line 1, Claim 8: Please correct "mecA" to read -- *mecA* --

Column 49, Line 2, Claim 8: Please correct "mecA" to read -- *mecA* --

CERTIFICATE OF CORRECTION (continued)
U.S. Pat. No. 10,829,825 B2

Column 49, Line 4, Claim 8: Please correct "mecA" to read -- *mecA* --

Column 49, Line 10, Claim 9: Please correct "SCCmec" to read -- SCC*mec* --

Column 49, Line 11, Claim 9: Please correct "SCCmec" to read -- SCC*mec* --

Column 49, Line 12, Claim 9: Please correct "tnecA variant" to read -- *mecA variant* --

Column 49, Line 21, Claim 9: Please correct "mecA variant" to read -- *mecA variant* --

Column 49, Line 48, Claim 10: Please correct "SCCmec" to read -- SCC*mec* --

Column 49, Line 49, Claim 10: Please correct "SCCmec" to read -- SCC*mec* --

Column 49, Line 50, Claim 10: Please correct "mecA or a mecA variant" to read -- *mecA* or a *mecA variant* --

Column 49, Line 53, Claim 10: Please correct "mecA variant" to read -- *mecA variant* --

Column 49, Line 54, Claim 10: Please correct "mecA variant" to read -- *mecA variant* --

Column 49, Line 56, Claim 10: Please correct "mecA variant" to read -- *mecA variant* --

Column 49, Line 58, Claim 10: Please correct "mecA variant" to read -- *mecA variant* --

Column 49, Line 66, Claim 10: Please correct "mecA" to read -- *mecA* --

Column 49, Line 67, Claim 10: Please correct "mecA" to read -- *mecA* --

Column 50, Line 1, Claim 10: Please correct "mecA" to read -- *mecA* --

Column 50, Line 2, Claim 10: Please correct "mecA" to read -- *mecA* --

Column 50, Line 7, Claim 11: Please correct "mecA variant" to read -- *mecA variant* --

Column 50, Line 10, Claim 11: Please correct "mecA variant" to read -- *mecA variant* --

Column 50, Line 11, Claim 11: Please correct "tnecA variant" to read -- *mecA variant* --

Column 50, Line 13, Claim 12: Please correct "mecA" to read -- *mecA* --

Column 50, Line 15, Claim 12: Please correct "mecA" to read -- *mecA* --

Column 50, Line 16, Claim 12: Please correct "mecA" to read -- *mecA* --

Column 50, Line 18, Claim 13: Please correct "mecA variant" to read -- *mecA variant* --

CERTIFICATE OF CORRECTION (continued)
U.S. Pat. No. 10,829,825 B2

Column 50, Line 22, Claim 14: Please correct "mecA variant" to read -- *mecA variant* --

Column 50, Line 27, Claim 15: Please correct "mecA variant" to read -- *mecA variant* --

Column 50, Line 31, Claim 16: Please correct "mecA variant" to read -- *mecA variant* --

Column 50, Line 32, Claim 16: Please correct "mecA$_{LGA251}$" to read -- *mecA*$_{LGA251}$ --

Column 50, Line 35, Claim 17: Please correct "SCCmec" to read -- SCC*mec* --

Column 50, Line 36, Claim 17: Please correct "SCCmec" to read -- SCC*mec* --

Column 50, Line 37, Claim 17: Please correct "mecA or a mecA variant" to read -- *mecA* or a *mecA variant* --

Column 50, Line 40, Claim 17: Please correct "mecA variant" to read -- *mecA variant* --

Column 50, Line 41, Claim 17: Please correct "mecA variant" to read -- *mecA variant* --

Column 50, Line 43, Claim 17: Please correct "mecA variant" to read -- *mecA variant* --

Column 50, Line 45, Claim 17: Please correct "mecA variant" to read -- *mecA variant* --

Column 50, Line 53, Claim 17: Please correct "mecA" to read -- *mecA* --

Column 50, Line 54, Claim 17: Please correct "mecA" to read -- *mecA* --

Column 50, Line 55, Claim 17: Please correct "mecA" to read -- *mecA* --

Column 50, Line 56, Claim 17: Please correct "mecA" to read -- *mecA* --

Column 50, Line 64, Claim 17: Please correct "SCCmec" to read -- SCC*mec* --

Column 50, Line 65, Claim 17: Please correct "comprising" to read -- comprising *mecA,* --

Column 51, Line 15, Claim 19: Please correct "SCCmec" to read -- SCC*mec* --

Column 51, Line 16, Claim 19: Please correct "SCCmec" to read -- SCC*mec* --

Column 51, Line 17, Claim 19: Please correct "mecA or a mecA variant" to read -- *mecA* or a *mecA variant* --

Column 51, Line 20, Claim 19: Please correct "mecA variant" to read -- *mecA variant* --

Column 51, Line 21-22, Claim 19: Please correct "mecA variant" to read -- *mecA variant* --

CERTIFICATE OF CORRECTION (continued)
U.S. Pat. No. 10,829,825 B2

Column 51, Line 23, Claim 19: Please correct "mecA variant" to read -- *mecA variant* --

Column 51, Line 25, Claim 19: Please correct "mecA variant" to read -- *mecA variant* --

Column 52, Line 4, Claim 19: Please correct "mecA" to read -- *mecA* --

Column 52, Line 5, Claim 19: Please correct "mecA" to read -- *mecA* --

Column 52, Line 6, Claim 19: Please correct "mecA" to read -- *mecA* --

Column 52, Line 7, Claim 19: Please correct "mecA" to read -- *mecA* --

SEQUENCE LISTING

<160> NUMBER OF SEQ ID NOS: 30

<210> SEQ ID NO 1
<211> LENGTH: 19
<212> TYPE: DNA
<213> ORGANISM: Artificial Sequence
<220> FEATURE:
<223> OTHER INFORMATION: Oligonucleotide mecAv-orfX-1

<400> SEQUENCE: 1
atgaagcaat atcaaagga                                    19

<210> SEQ ID NO 2
<211> LENGTH: 19
<212> TYPE: DNA
<213> ORGANISM: Artificial Sequence
<220> FEATURE:
<223> OTHER INFORMATION: Oligonucleotide mecAv-orfX-2

<400> SEQUENCE: 2
tgaagcaata tcaaaggaa                                    19

<210> SEQ ID NO 3
<211> LENGTH: 30
<212> TYPE: DNA
<213> ORGANISM: Artificial Sequence
<220> FEATURE:
<223> OTHER INFORMATION: Oligonucleotide mecAv-orfX-3

<400> SEQUENCE: 3
ataacttggt tattcaaaga tgacgatatt                        30

<210> SEQ ID NO 4
<211> LENGTH: 29
<212> TYPE: DNA
<213> ORGANISM: Artificial Sequence
<220> FEATURE:
<223> OTHER INFORMATION: Oligonucleotide mecAv-orfX-4

<400> SEQUENCE: 4
acttggttat tcaaagatga cgatattga                              29

<210> SEQ ID NO 5
<211> LENGTH: 28
<212> TYPE: DNA
<213> ORGANISM: Artificial Sequence
<220> FEATURE:
<223> OTHER INFORMATION: Oligonucleotide mecAv-orfX-5

<400> SEQUENCE: 5
tggttattca agatgacga tattgaga                                28

<210> SEQ ID NO 6
<211> LENGTH: 21
<212> TYPE: DNA
<213> ORGANISM: Artificial Sequence
<220> FEATURE:
<223> OTHER INFORMATION: Oligonucleotide mecAv-orfX-6

<400> SEQUENCE: 6
atcctaatat gttaatggcg a                                      21

<210> SEQ ID NO 7
<211> LENGTH: 20
<212> TYPE: DNA
<213> ORGANISM: Artificial Sequence
<220> FEATURE:
<223> OTHER INFORMATION: Oligonucleotide mecAv-orfX-7

<400> SEQUENCE: 7
atggcgatta atgttaaaga                                        20

<210> SEQ ID NO 8
<211> LENGTH: 29
<212> TYPE: DNA
<213> ORGANISM: Artificial Sequence
<220> FEATURE:
<223> OTHER INFORMATION: Oligonucleotide mecAv-orfX-8

<400> SEQUENCE: 8
tggccagcta taatgctact atatctgga                              29

<210> SEQ ID NO 9
<211> LENGTH: 25
<212> TYPE: DNA
<213> ORGANISM: Artificial Sequence
<220> FEATURE:
<223> OTHER INFORMATION: Oligonucleotide mecAv-orfX-9

<400> SEQUENCE: 9
tcagcaaaat gacatttcca catca                                  25

<210> SEQ ID NO 10
<211> LENGTH: 25
<212> TYPE: DNA
<213> ORGANISM: Artificial Sequence
<220> FEATURE:

<223> OTHER INFORMATION: Oligonucleotide mecAv-orfX-10

<400> SEQUENCE: 10
tcagcaaaat gacattccca catca                                    25

<210> SEQ ID NO 11
<211> LENGTH: 29
<212> TYPE: DNA
<213> ORGANISM: Artificial Sequence
<220> FEATURE:
<223> OTHER INFORMATION: Oligonucleotide mecAv-orfX-11

<400> SEQUENCE: 11
tgatgcgggt tgtgttaatt garcaagtg                                29

<210> SEQ ID NO 12
<211> LENGTH: 22
<212> TYPE: DNA
<213> ORGANISM: Artificial Sequence
<220> FEATURE:
<223> OTHER INFORMATION: Oligonucleotide mecA-1

<400> SEQUENCE: 12
accttctaca cctccatatc ac                                       22

<210> SEQ ID NO 13
<211> LENGTH: 20
<212> TYPE: DNA
<213> ORGANISM: Artificial Sequence
<220> FEATURE:
<223> OTHER INFORMATION: Oligonucleotide mecA-2

<400> SEQUENCE: 13
cgttacggat tgcttcactg                                          20

<210> SEQ ID NO 14
<211> LENGTH: 25
<212> TYPE: DNA
<213> ORGANISM: Artificial Sequence
<220> FEATURE:
<223> OTHER INFORMATION: Oligonucleotide mecAv-1

<400> SEQUENCE: 14
aacactgatg gttttaaggt atcca                                    25

<210> SEQ ID NO 15
<211> LENGTH: 29
<212> TYPE: DNA
<213> ORGANISM: Artificial Sequence
<220> FEATURE:
<223> OTHER INFORMATION: Oligonucleotide mecAv-2

<400> SEQUENCE: 15
aaggtatcca ttgcaaatac ttatgacaa                                29

<210> SEQ ID NO 16
<211> LENGTH: 29
<212> TYPE: DNA
<213> ORGANISM: Artificial Sequence
<220> FEATURE:
<223> OTHER INFORMATION: Oligonucleotide mecAv-3

<400> SEQUENCE: 16
taccagatcc atcgtcattt ttcatatgt                                29

```
<210> SEQ ID NO 17
<211> LENGTH: 27
<212> TYPE: DNA
<213> ORGANISM: Artificial Sequence
<220> FEATURE:
<223> OTHER INFORMATION: Oligonucleotide mecAv-4

<400> SEQUENCE: 17
taccagatcc atcgtcattt ttcatat                                         27

<210> SEQ ID NO 18
<211> LENGTH: 26
<212> TYPE: DNA
<213> ORGANISM: Artificial Sequence
<220> FEATURE:
<223> OTHER INFORMATION: Oligonucleotide mecAv-5

<400> SEQUENCE: 18
attggagaaa aaggctgaaa acggaa                                          26

<210> SEQ ID NO 19
<211> LENGTH: 30
<212> TYPE: DNA
<213> ORGANISM: Artificial Sequence
<220> FEATURE:
<223> OTHER INFORMATION: Oligonucleotide mecAv-6

<400> SEQUENCE: 19
attggagaaa aaggctgaaa acggaaaaga                                      30

<210> SEQ ID NO 20
<211> LENGTH: 20
<212> TYPE: DNA
<213> ORGANISM: Artificial Sequence
<220> FEATURE:
<223> OTHER INFORMATION: Oligonucleotide mecAv-7

<400> SEQUENCE: 20
ccagatatag tagcattata                                                 20

<210> SEQ ID NO 21
<211> LENGTH: 18
<212> TYPE: DNA
<213> ORGANISM: Artificial Sequence
<220> FEATURE:
<223> OTHER INFORMATION: Oligonucleotide mecAv-8

<400> SEQUENCE: 21
aaagatgacg atattgag                                                   18

<210> SEQ ID NO 22
<211> LENGTH: 20
<212> TYPE: DNA
<213> ORGANISM: Artificial Sequence
<220> FEATURE:
<223> OTHER INFORMATION: Oligonucleotide mecA-mecAv-1

<400> SEQUENCE: 22
tcaccaggtt caacycaaaa                                                 20

<210> SEQ ID NO 23
<211> LENGTH: 23
<212> TYPE: DNA
<213> ORGANISM: Artificial Sequence
<220> FEATURE:
<223> OTHER INFORMATION: Oligonucleotide mecA-mecAv-2
```

-continued

```
<400> SEQUENCE: 23
cctgaatcwg ctaataatat ttc                                           23

<210> SEQ ID NO 24
<211> LENGTH: 18
<212> TYPE: DNA
<213> ORGANISM: Artificial Sequence
<220> FEATURE:
<223> OTHER INFORMATION: Oligonucleotide S.aureus-1

<400> SEQUENCE: 24
cacctgctgc aaatgctg                                                 18

<210> SEQ ID NO 25
<211> LENGTH: 29
<212> TYPE: DNA
<213> ORGANISM: Artificial Sequence
<220> FEATURE:
<223> OTHER INFORMATION: Oligonucleotide S.aureus-2

<400> SEQUENCE: 25
cgttgatcag crtttaagtt aggcatatt                                     29

<210> SEQ ID NO 26
<211> LENGTH: 28
<212> TYPE: DNA
<213> ORGANISM: Artificial Sequence
<220> FEATURE:
<223> OTHER INFORMATION: Oligonucleotide S.aureus-3

<400> SEQUENCE: 26
cgcaacacga tgaagctcaa caaaatgc                                      28

<210> SEQ ID NO 27
<211> LENGTH: 26
<212> TYPE: DNA
<213> ORGANISM: Artificial Sequence
<220> FEATURE:
<223> OTHER INFORMATION: Oligonucleotide S.aureus-4

<400> SEQUENCE: 27
ggtgtagaga aatatggtcc tgaagc                                        26

<210> SEQ ID NO 28
<211> LENGTH: 23
<212> TYPE: DNA
<213> ORGANISM: Artificial Sequence
<220> FEATURE:
<223> OTHER INFORMATION: Oligonucleotide S.aureus-5

<400> SEQUENCE: 28
gtcctgaagc aagtgcattt acg                                           23

<210> SEQ ID NO 29
<211> LENGTH: 31
<212> TYPE: DNA
<213> ORGANISM: Artificial Sequence
<220> FEATURE:
<223> OTHER INFORMATION: Oligonucleotide S.aureus-6

<400> SEQUENCE: 29
ggacgtggct tagcgtatat ttatgctgat g                                  31

<210> SEQ ID NO 30
<211> LENGTH: 22
```

```
<212> TYPE: DNA
<213> ORGANISM: Artificial Sequence
<220> FEATURE:
<223> OTHER INFORMATION: Oligonucleotide S.aureus-7

<400> SEQUENCE: 30
gcaactttag ccaagccttg ac                                                  22
```